United States Patent
Compton et al.

(10) Patent No.: US 8,673,010 B2
(45) Date of Patent: Mar. 18, 2014

(54) FLEXIBLE CHAIN IMPLANTS AND INSTRUMENTATION

(75) Inventors: Curtis Compton, Downingtown, PA (US); Dennis Chien, West Chester, PA (US); Robert Delurio, Aston, PA (US); Dominique Messerli, Downingtown, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 969 days.

(21) Appl. No.: 12/601,468

(22) PCT Filed: Jun. 30, 2008

(86) PCT No.: PCT/US2008/068836
§ 371 (c)(1),
(2), (4) Date: Nov. 23, 2009

(87) PCT Pub. No.: WO2009/006432
PCT Pub. Date: Jan. 8, 2009

(65) Prior Publication Data
US 2010/0185290 A1 Jul. 22, 2010

Related U.S. Application Data

(60) Provisional application No. 60/947,258, filed on Jun. 29, 2007.

(51) Int. Cl.
*A61F 2/44* (2006.01)
(52) U.S. Cl.
USPC .................................. 623/17.16; 623/17.11
(58) Field of Classification Search
USPC ........................................ 623/17.11, 17.16
See application file for complete search history.

(56) References Cited

U.S. PATENT DOCUMENTS

| 2,659,369 A | 11/1952 | Lipman |
| 4,839,215 A | 6/1989 | Starling et al. |

(Continued)

FOREIGN PATENT DOCUMENTS

| DE | 10309986 | 9/2004 |
| GB | 2 237 564 | 5/1991 |

(Continued)

OTHER PUBLICATIONS

PCT Written Opinion of the International Searching Authority.

(Continued)

*Primary Examiner* — Nicholas Woodall
*Assistant Examiner* — Christine Nelson
(74) *Attorney, Agent, or Firm* — Baker & Hostetler LLP

(57) ABSTRACT

A flexible chain implant for insertion into an interior volume of a vertebral body. The implant may be implanted in an insertion position for sliding through a cannula and is flexible for packing into the interior volume in an implanted configuration. The implant randomly separates in the implanted configuration. The implant includes a top member and a bottom member, wherein the top and bottom members are coupled to one another at a coupled portion. The top and bottom members preferably each include an inner surface such that the inner surfaces include a plurality of alternating projections and recesses so that the projections are received within the recesses in an insertion position. Alternatively, the implant may include a plurality of substantially non-flexible bodies and a plurality of substantially flexible links interconnecting the bodies. The non-flexible bodies include a plurality of facets and/or abutment surfaces.

12 Claims, 12 Drawing Sheets

(56) References Cited

U.S. PATENT DOCUMENTS

| | | |
|---|---|---|
| 5,522,894 A | 6/1996 | Draenert |
| 5,534,023 A | 7/1996 | Henley |
| 5,702,454 A | 12/1997 | Baumgartner |
| 5,755,797 A | 5/1998 | Baumgartner |
| 5,756,127 A | 5/1998 | Grisoni et al. |
| 5,843,189 A | 12/1998 | Perouse |
| 5,958,465 A | 9/1999 | Klemm et al. |
| 5,961,554 A | 10/1999 | Janson et al. |
| 6,183,768 B1 | 2/2001 | Härle |
| 6,206,923 B1 | 3/2001 | Boyd et al. |
| 6,387,130 B1 | 5/2002 | Stone et al. |
| 6,620,162 B2 | 9/2003 | Kuslich et al. |
| 6,632,235 B2 | 10/2003 | Weikel et al. |
| 6,652,593 B2 | 11/2003 | Boyer, II et al. |
| 6,776,800 B2 | 8/2004 | Boyer, II et al. |
| 6,855,169 B2 | 2/2005 | Boyer, II et al. |
| 7,238,209 B2 | 7/2007 | Matsuzaki et al. |
| 7,351,262 B2 | 4/2008 | Bindseil et al. |
| 2003/0060892 A1 | 3/2003 | Richter et al. |
| 2004/0052829 A1 | 3/2004 | Shimp |
| 2004/0097930 A1 | 5/2004 | Justis et al. |
| 2004/0249464 A1 | 12/2004 | Bindseil et al. |
| 2005/0027366 A1 | 2/2005 | Saini et al. |
| 2005/0113855 A1 | 5/2005 | Kennedy, II et al. |
| 2005/0113918 A1* | 5/2005 | Messerli et al. ........... 623/17.11 |
| 2005/0131548 A1 | 6/2005 | Boyer, II et al. |
| 2005/0209629 A1 | 9/2005 | Kerr et al. |
| 2005/0209695 A1 | 9/2005 | De Vries et al. |
| 2005/0278023 A1 | 12/2005 | Zwirkoski |
| 2006/0052874 A1 | 3/2006 | Johnson et al. |
| 2006/0089715 A1 | 4/2006 | Truckai et al. |
| 2006/0100304 A1 | 5/2006 | Vresilovic et al. |
| 2006/0265077 A1 | 11/2006 | Zwirkoski |
| 2007/0016213 A1 | 1/2007 | Robie et al. |
| 2007/0055274 A1 | 3/2007 | Appenzeller et al. |
| 2007/0093822 A1 | 4/2007 | Dutoit et al. |
| 2007/0093846 A1 | 4/2007 | Frigg et al. |
| 2007/0093899 A1 | 4/2007 | Dutoit et al. |
| 2007/0093912 A1 | 4/2007 | Borden |
| 2007/0123986 A1 | 5/2007 | Schaller |
| 2007/0149978 A1 | 6/2007 | Shezifi et al. |
| 2007/0162132 A1 | 7/2007 | Messerli |
| 2007/0233146 A1 | 10/2007 | Henniges et al. |
| 2007/0260313 A1 | 11/2007 | Sidler |
| 2007/0270955 A1 | 11/2007 | Chow |
| 2008/0133012 A1 | 6/2008 | McGuckin |
| 2008/0306595 A1 | 12/2008 | McLeod et al. |

FOREIGN PATENT DOCUMENTS

| | | |
|---|---|---|
| WO | WO 86/03671 | 7/1986 |
| WO | WO 95/25483 | 9/1995 |
| WO | WO 2006/072941 | 7/2006 |
| WO | WO 2007/140315 | 12/2007 |

OTHER PUBLICATIONS

PCT International Search Report dated May 18, 2009.

* cited by examiner

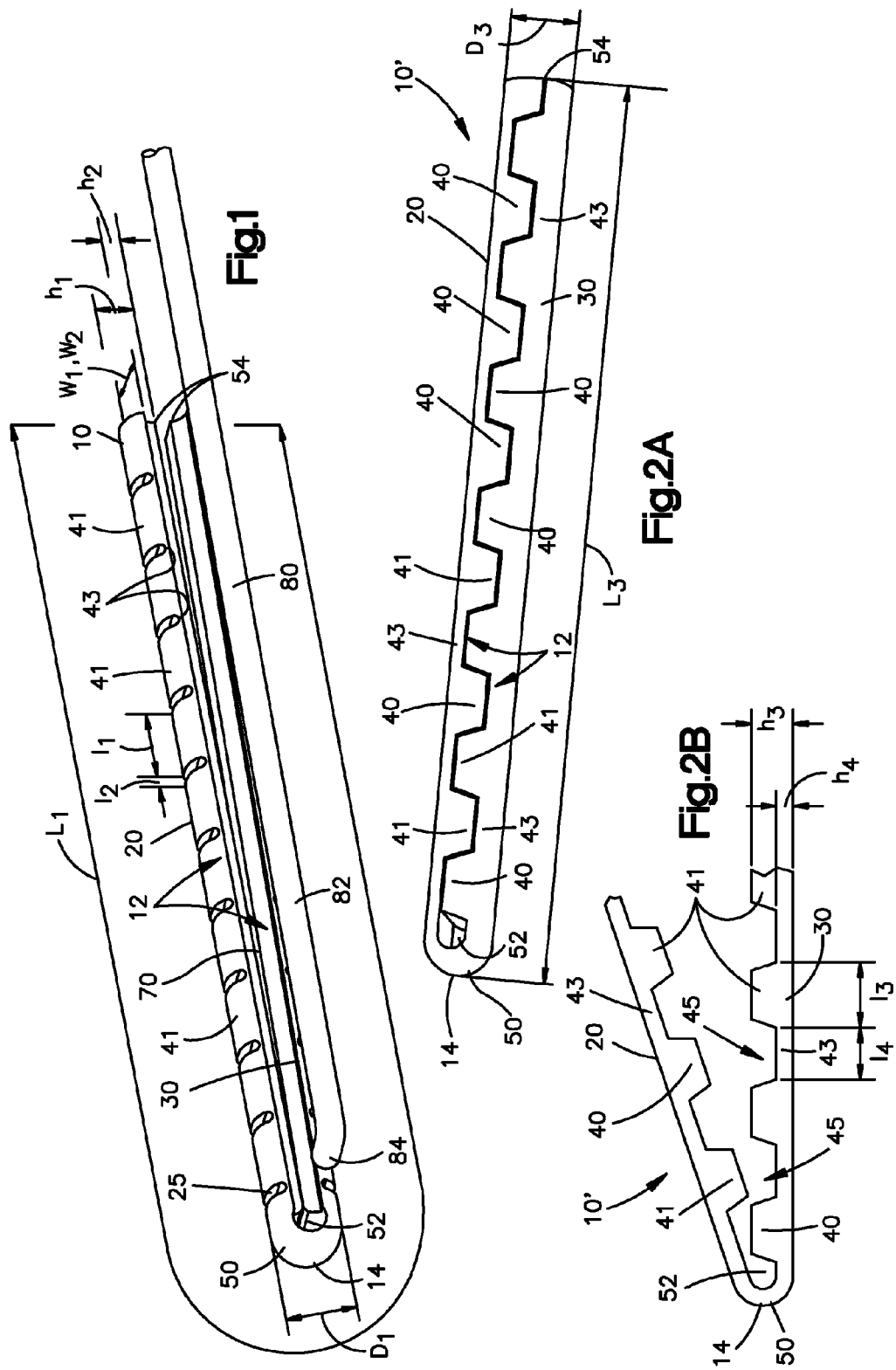

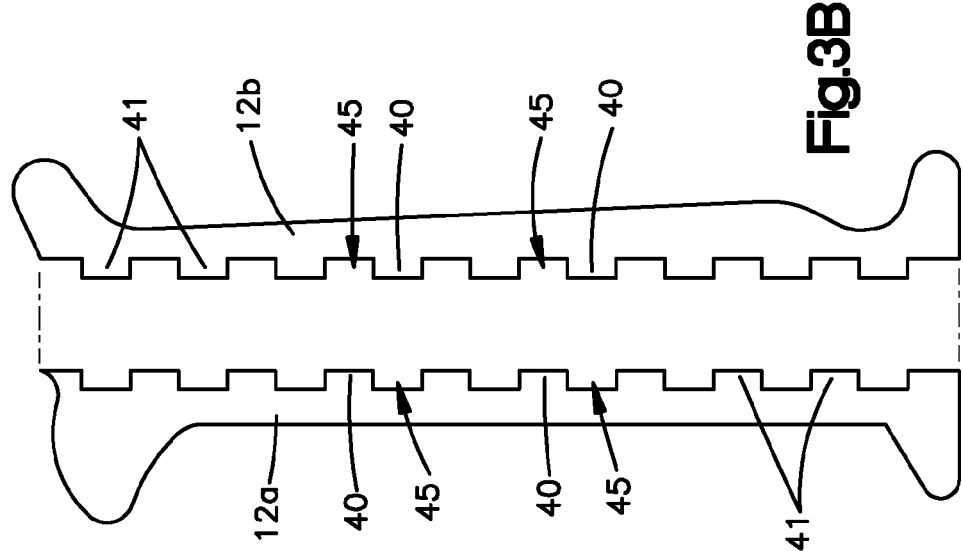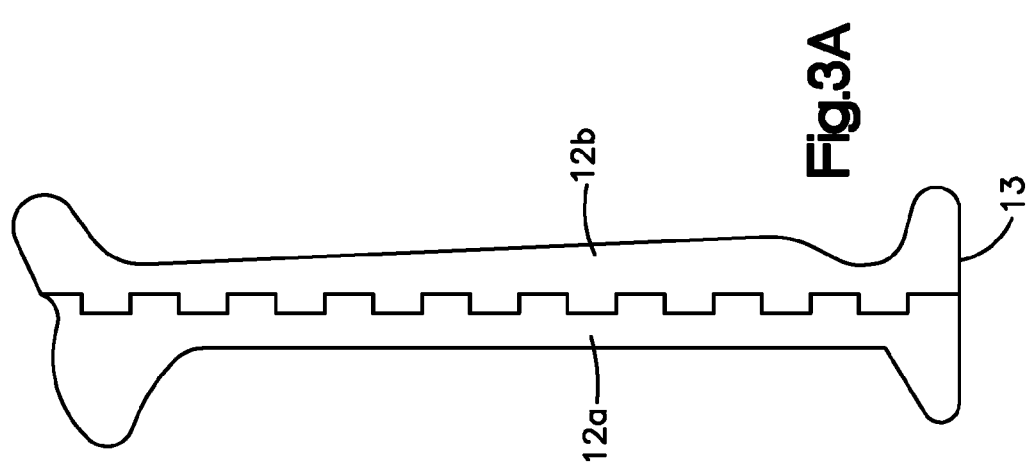

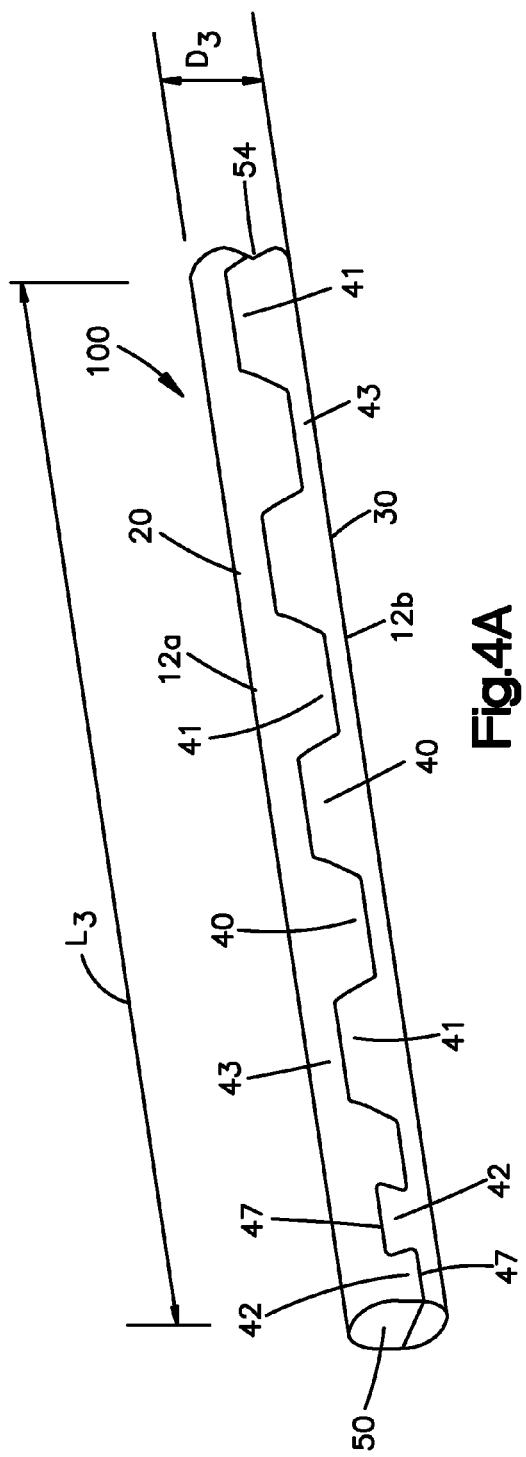
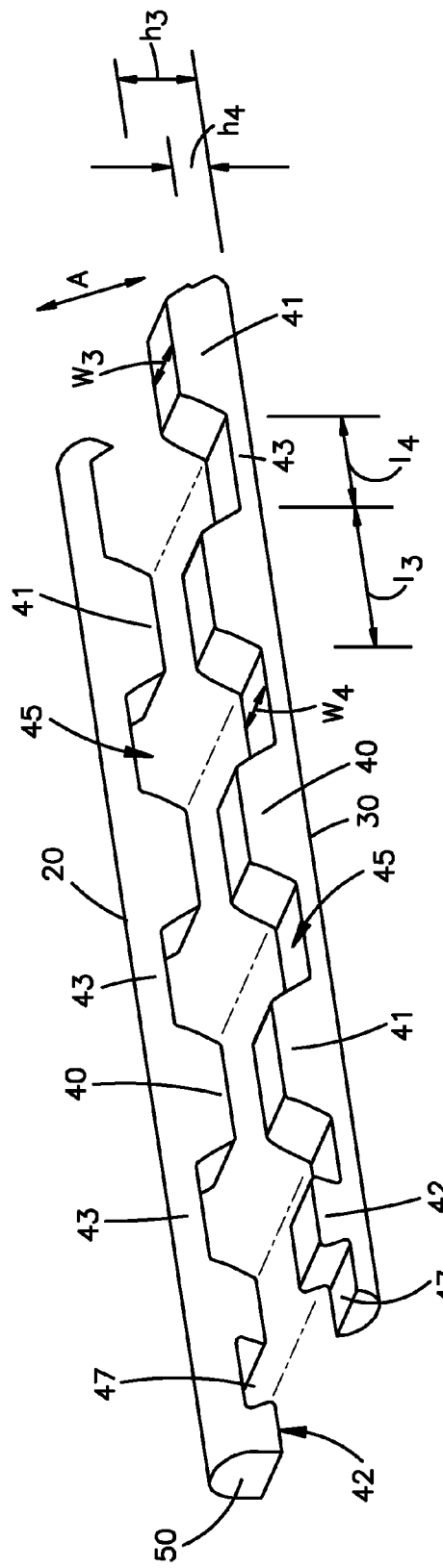
Fig.4A
Fig.4B

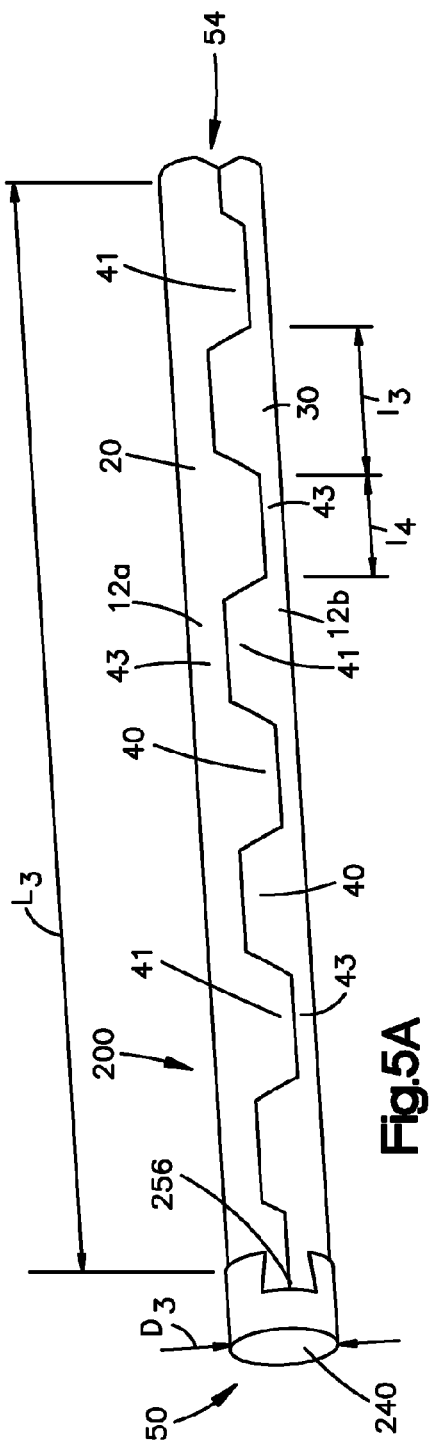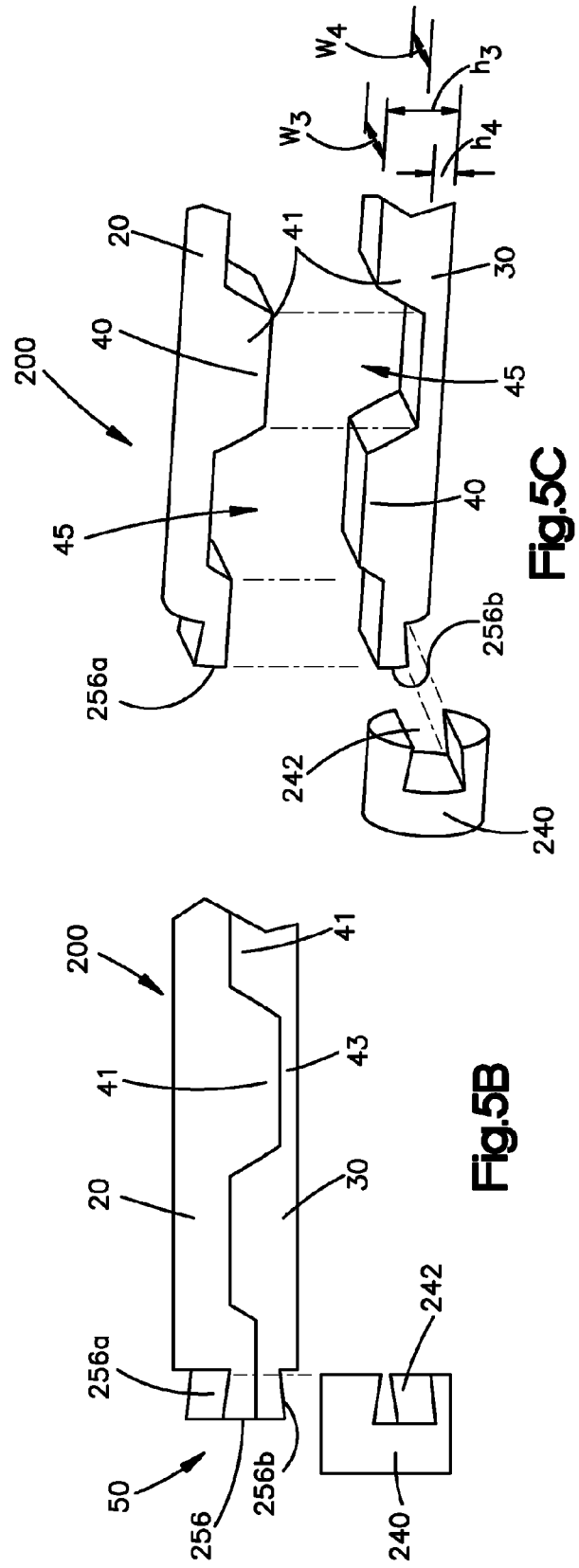

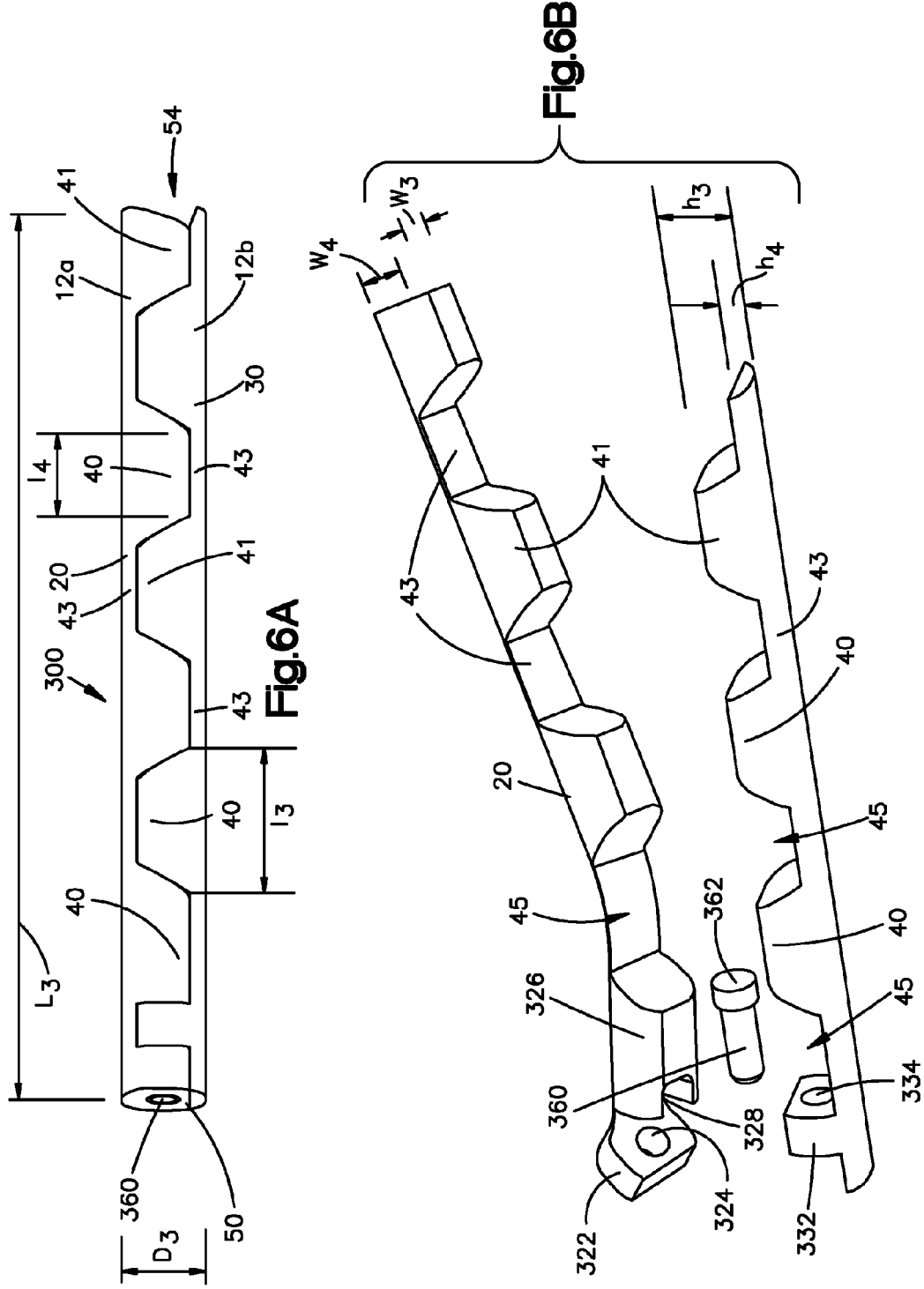

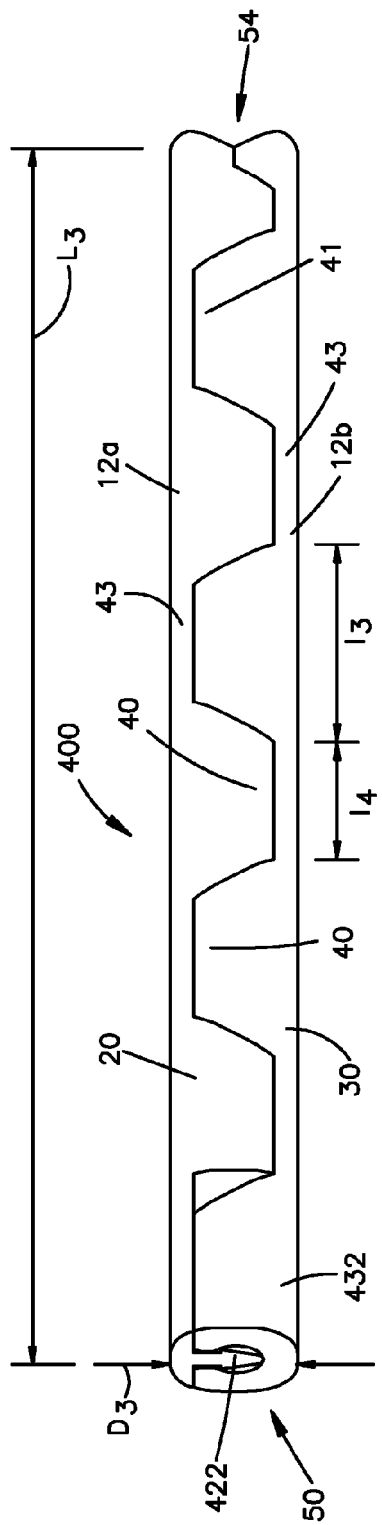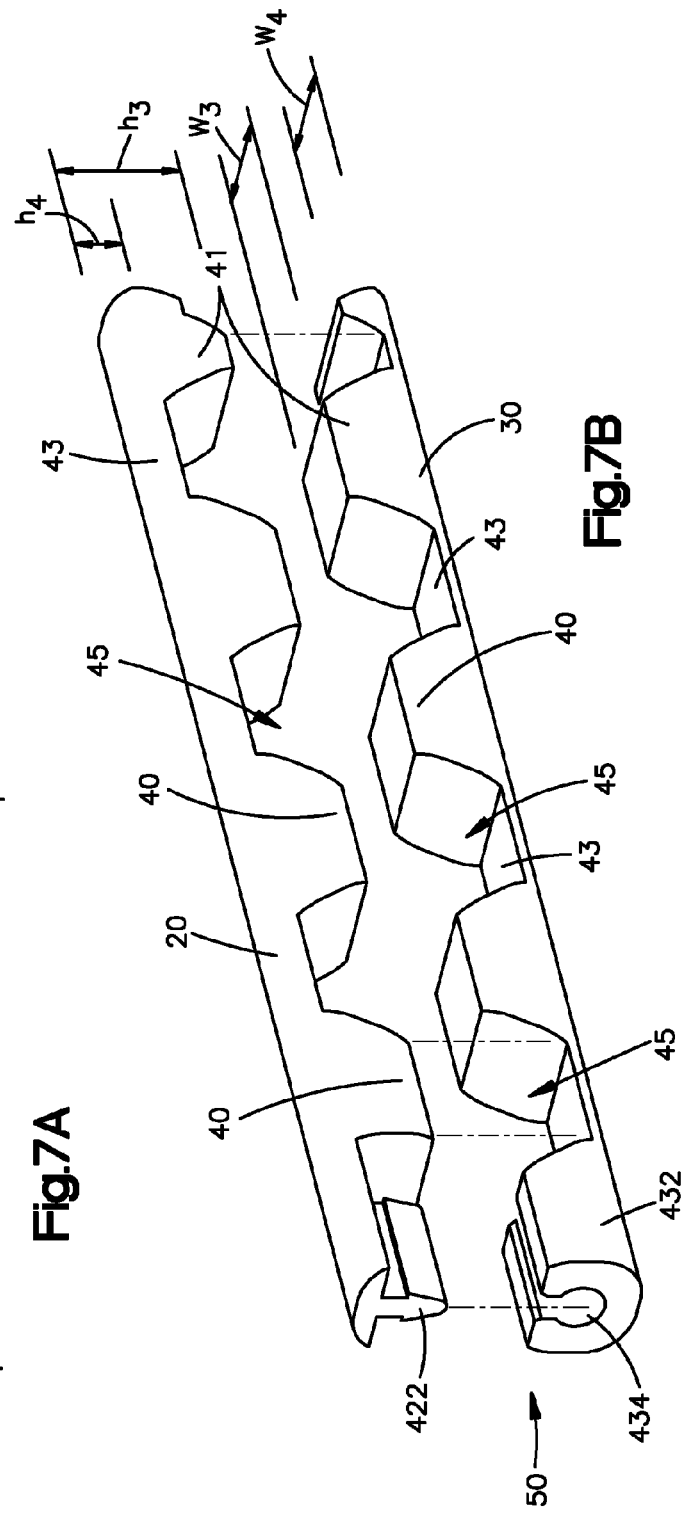

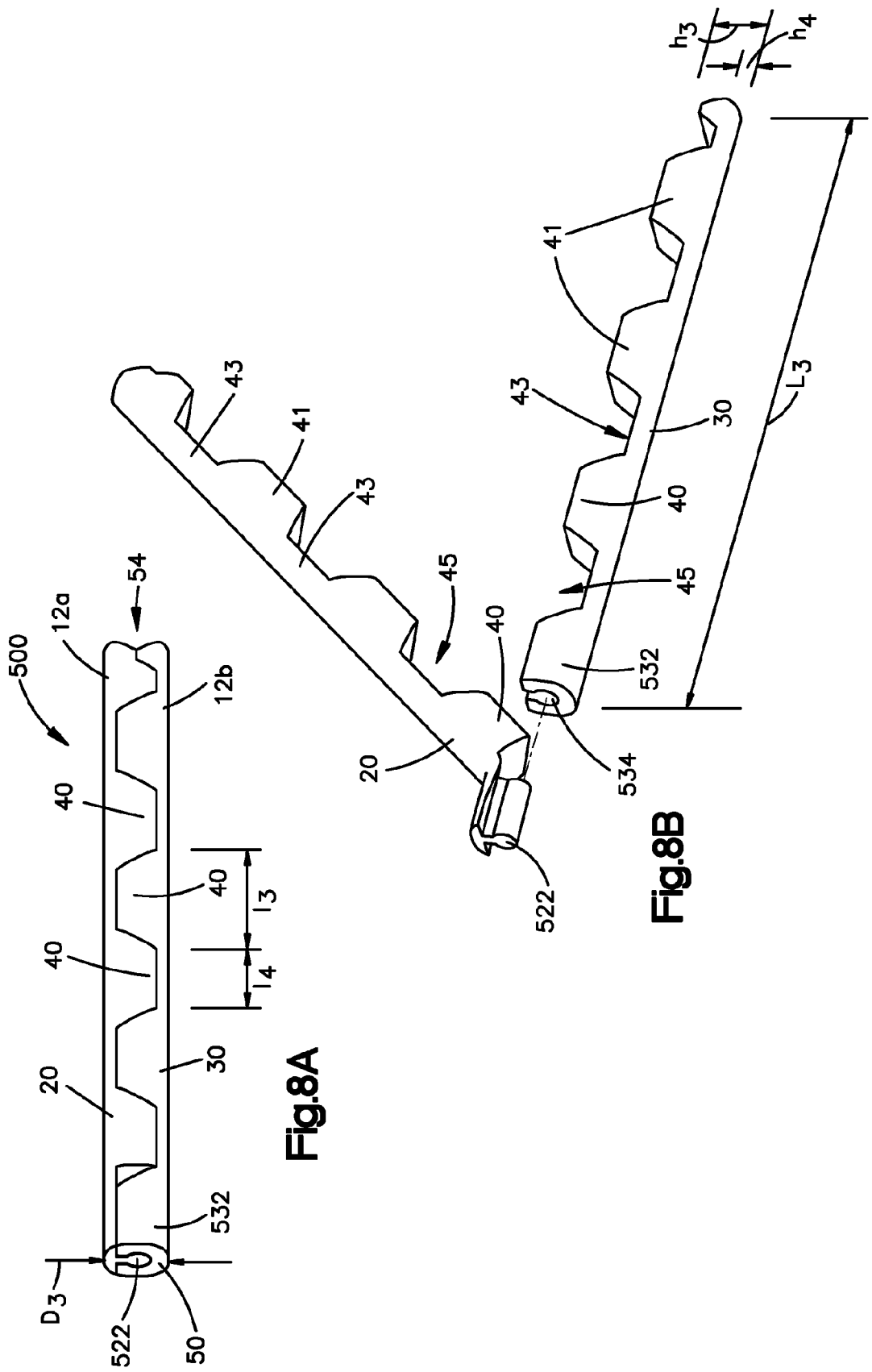

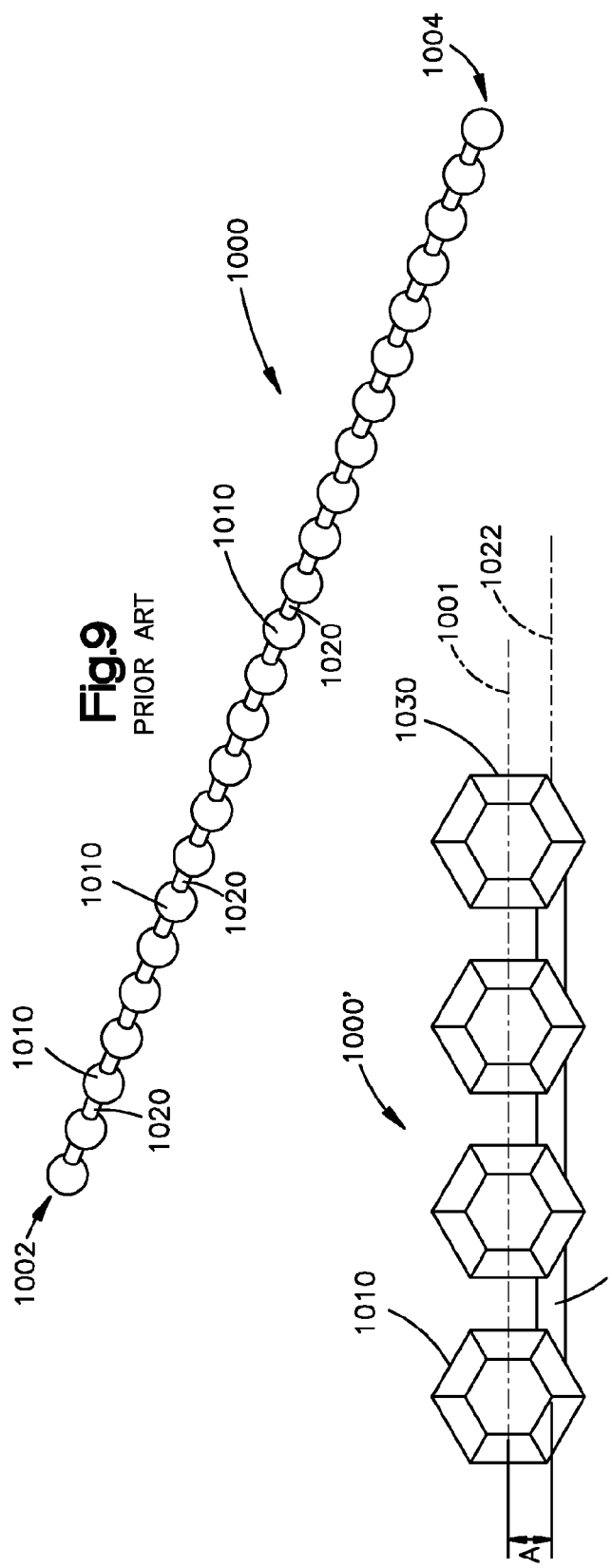

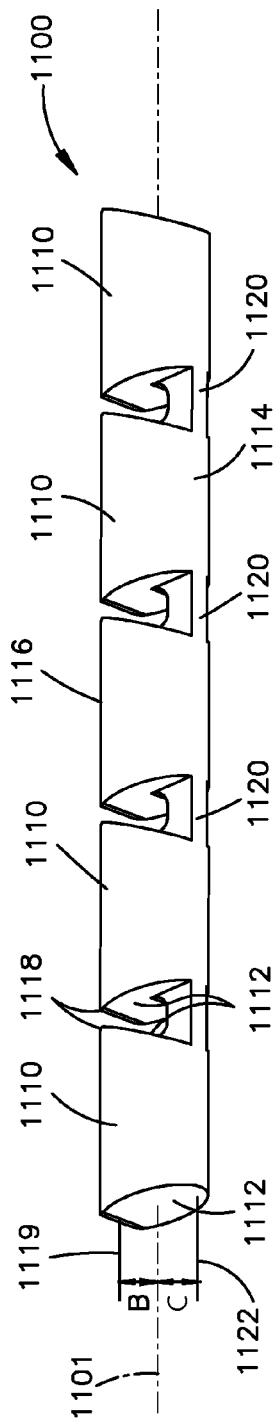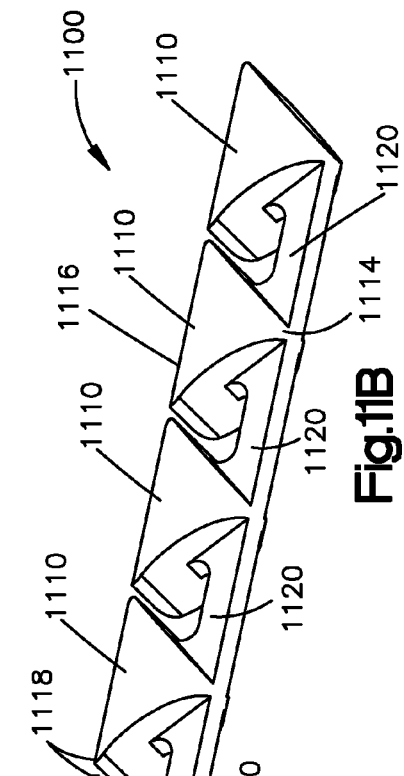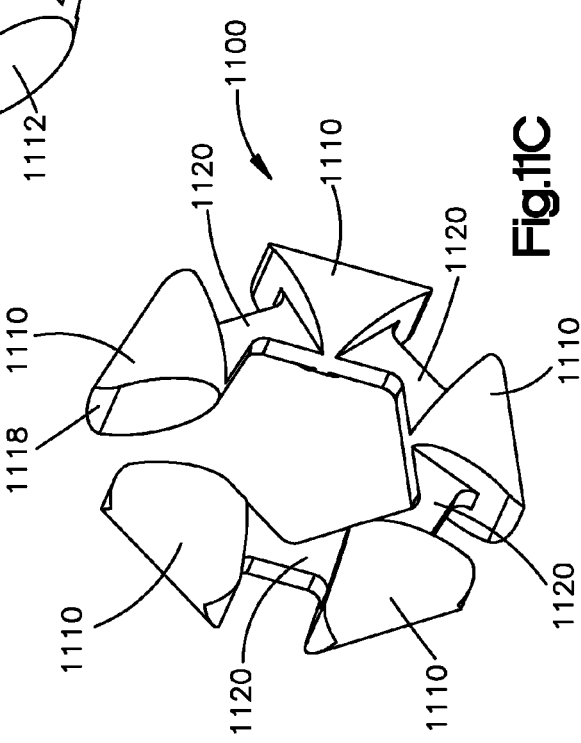

FLEXIBLE CHAIN IMPLANTS AND INSTRUMENTATION

CROSS REFERENCE TO RELATED APPLICATIONS

This application is the national phase application of PCT Application No. PCT/US2008/068836, filed Jun. 30, 2008, which claims the benefit of U.S. Provisional Application No. 60/947,258, filed on Jun. 29, 2007, titled "Flexible Chain, Implants and Instrumentation," the contents of which is hereby incorporated by reference in its entirety.

FIELD OF THE INVENTION

The invention relates to implants, and more particularly to implants for augmenting or supporting bones or other structures, such as, for example, a vertebral body.

BACKGROUND OF THE INVENTION

Vertebral compression fractures ("VCF") represent a common spinal injury and may result in prolonged disability. Generally speaking, VCF involves collapsing of one or more vertebral bodies in the spine. VCF usually occurs in the lower vertebrae of the thoracic spine or the upper vertebrae of the lumbar spine. VCF generally involves fracture of the anterior portion of the affected vertebral body. VCF may result in deformation of the normal alignment or curvature, e.g., lordosis, of the vertebral bodies in the affected area of the spine. VCF and/or related spinal deformities may result, for example, from metastatic diseases of the spine, from trauma or may be associated with osteoporosis. Until recently, doctors were limited in how they could treat VCF and related deformities.

Recently, minimally invasive surgical procedures for treating VCF have been developed. These procedures generally involve the use of a cannula or other access tool inserted into the posterior of the targeted vertebral body, usually through the pedicles.

In one such procedure, a cannula or bone needle is passed through the soft tissue of the patient's back. Once properly positioned, a small amount of polymethylmethacrylate (PMMA) or other orthopedic cement is pushed through the needle into the targeted vertebral body. This technique may be effective in the reduction or elimination of fracture pain, prevention of further collapse, and a return to mobility in patients. However, this technique typically does not reposition the fractured bone into its original size and/or shape and, therefore, may not address the problem of spinal deformity due to the fracture.

Other treatments for VCF generally involve two phases: (1) reposition, or restoration of the original height of the vertebral body and consequent lordotic correction of the spinal curvature; and (2) augmentation, or addition of material to support or strengthen the fractured or collapsed vertebral body.

One such treatment involves inserting, through a cannula, a catheter having an expandable member into an interior volume of a fractured vertebral body, wherein the interior volume has a relatively soft cancellous bone surrounded by fractured cortical bone therein. The expandable member is expanded within the interior volume in an attempt to restore the vertebral body towards its original height. The expandable member is removed from the interior volume, leaving a void within the vertebral body. PMMA or other filler material is injected through the cannula into the void to stabilize the vertebral body. The cannula is then removed and the cement cures to augment, fill or fix the vertebral body.

Another approach for treating VCF involves inserting an expandable mesh graft balloon, or containment device, into the targeted vertebral body. The graft balloon remains inside the vertebral body after it is inflated with PMMA or an allograft product, which limits intraoperative loss of height of the repositioned endplates.

In some cases of fractured or otherwise damaged bones, bone grafts may be used to repair or otherwise treat the damaged area. In the United States alone, approximately half a million bone grafting procedures are performed annually, directed to a diverse array of medical interventions for complications such as fractures involving bone loss, injuries or other conditions necessitating immobilization by fusion (such as for the spine or joints), and other bone defects that may be present due to trauma, infection, or disease. Bone grafting involves the surgical transplantation of pieces of bone within the body, and generally is effectuated through the use of graft material acquired from a human source. Human graft material is primarily utilized due to the limited applicability of xenografts, e.g., transplants from another species.

Many orthopedic procedures involve the use of allografts, which are bone grafts from other human sources (normally cadavers). Allografts, for example, are placed in a host bone and serve as the substructure for supporting new bone tissue growth from the host bone.

The various bones of the human body such as the femur (thigh), tibia and fibula (leg), humerus (upper arm), radius and ulna (lower arm) have geometries that vary considerably. The lengths of these bones are varied, as well as the shape of the cross section of each type of bone and the shape of any given bone over its length. In addition, the wall thickness may vary in different areas of the cross-section of each bone. Thus, the use of any given bone to produce an implant or a component of an implant may be a function of the donor bone's dimensions and geometry. Machining of bones, however, may permit the production of an implant or a component of an implant with standardized or custom dimensions. Further, the availability of allograft bone source material is limited and the ability to enhance the bone yield from the available supply of allograft bone material is desirable.

As shown in FIG. 9 and as generally described in U.S. patent application Ser. No. 11/633,131, entitled "Flexible Elongated Chain Implant and Method of Supporting Body and Tissue With Same", the entire contents of which are hereby incorporated by reference, a prior art flexible chain implant 1000 may include a plurality of bodies 1010 and a plurality of linking portions 1020 (sometimes referred to as struts, bridges or links). The implant 1000 comprises a single flexible monolithic chain having a first end 1002 and a second end 1004 formed of allograft cortical bone having a plurality of substantially non-flexible bodies connected by substantially flexible links. Such an implant 1000 may be utilized to treat VCF.

Thus, it is desirable in the art to provide safe and effective implants and methods for aiding and/or augmenting fractured or otherwise damaged vertebral bodies and other bones, preferably implants that may be inserted via a minimally invasive surgical technique. Moreover, where the implant is formed from bone, it is desirable to provide implants that are designed to enhance existing bone yield while minimizing discarded excess material.

BRIEF SUMMARY OF THE INVENTION

The present invention is preferably directed to an implant for insertion into an interior volume in a targeted vertebral body. The implant is preferably inserted into the vertebral body in a relatively compact insertion position and is oriented in an implanted configuration when located in the vertebral body so that the implant augments at least a portion of the interior volume of the targeted vertebral body so that large pockets or voids are limited within the interior volume, while small voids amenable to boney in-growth and providing a vascular pathway are provided. The implant preferably separates or unwraps from the insertion position and, generally, randomly coils and wraps or twists around itself and packs into in the implanted configuration. The implant is preferably sized and configured to be inserted into the targeted vertebral body via a minimally invasive surgical technique, such as, for example, through one or more cannulas via a transpedicular or extrapedicular approach.

In one exemplary embodiment, the implant has a coupled portion and a terminal end. The implant preferably also includes a top member and a bottom member wherein the top and bottom members are coupled to one another at the coupled portion. The top and bottom members include an inner surface. Each of the inner surfaces of the top and bottom members include a plurality of alternating projections and recesses so that, when in an insertion position, the projections formed in the top member are received within the recesses formed in the bottom member and the projections formed in the bottom member are received within the recesses formed in the top member. In the insertion position, the implant is preferably sized for receipt within a cannula. The top and bottom members preferably separate from one another to an implanted configuration as the implant is being inserted into and/or when the implant is positioned within the interior volume of the targeted vertebral body so that large pockets or voids are limited within the interior volume. Preferably the implant is constructed of bone, but may be constructed of a synthetic material.

In another exemplary embodiment, the implant includes a plurality of generally non-flexible bodies or nodules and a plurality of substantially flexible links interconnecting the plurality of bodies. Preferably, the bodies and links are connected end-to-end to form the implant. Each of the generally non-flexible bodies preferably includes a plurality of facets. The plurality of non-flexible bodies define a body axis and the plurality of links defining a link axis, each in an extended position, the body axis is off-set from the link axis in the extended position. Preferably the implant is formed from bone, but may be constructed of a synthetic material.

In another exemplary embodiment, the implant includes a plurality of generally non-flexible bodies or nodules and a plurality of substantially flexible links interconnecting the plurality of bodies. The plurality of links is preferably connected at their ends to one of the plurality of bodies to form the implant. Each of the plurality of bodies preferably includes a tapered surface having a wide end, a narrow end, and an abutment surface. The plurality of bodies define a longitudinal body axis and the plurality of links define a longitudinal link axis in an extended position. The longitudinal link axis is off-set from the longitudinal body axis. The abutment surface formed on each one of the plurality of bodies preferably further defines a longitudinal abutment axis. The longitudinal abutment axis is off-set from the longitudinal body axis and from the longitudinal link axis. Preferably the implant is formed from bone, but may be constructed of a synthetic material.

Other objects and features of the present invention will become apparent from the following detailed description, considered in conjunction with the accompanying drawing figures. It is to be understood, however, that the drawings are designed solely for the purpose of illustration and not as a definition of the limits of the invention, for which reference should be made to the appended claims.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the flexible chain implant of the present application, there is shown in the drawings preferred embodiments. The drawings are prepared from three-dimensional models of preferred embodiments of the flexible chain implant and related tooling and are accurate for making at least dimensional comparisons between various features of the preferred implants and related components. It should be understood, however, that the application is not limited to the precise arrangements and instrumentalities shown. In the drawings:

FIG. 1 is a top perspective view of a first preferred embodiment of a flexible chain implant having external cuts and a groove for receiving a rod;

FIG. 2A is a side perspective view of a second preferred embodiment of a flexible chain implant having alternating projections and recesses in an insertion position;

FIG. 2B is a side elevational view of the implant show in FIG. 2A, wherein a top member is spaced from a bottom member;

FIG. 3A is a side elevational view of a portion of bone cut to form alternating projections and recesses;

FIG. 3B is an exploded, side elevational view of the portion of bone shown in FIG. 3A;

FIG. 4A is a side perspective view of a third preferred embodiment of a multi-piece flexible chain implant, shown in an insertion position;

FIG. 4B is an exploded, side perspective view of the implant show in FIG. 4A;

FIG. 5A is a side perspective view of a fourth preferred embodiment of a multi-piece flexible chain implant, shown in an insertion position;

FIG. 5B is an enlarged, partially exploded, side perspective view of the implant show in FIG. 5A, showing a cap spaced from top and bottom members;

FIG. 5C is an exploded, side perspective view of the implant show in FIG. 5A;

FIG. 6A is a side perspective view of a fifth preferred embodiment of a multi-piece flexible chain implant, shown in an insertion position;

FIG. 6B is an exploded, side perspective view of the implant show in FIG. 6A;

FIG. 7A is a side perspective view of a sixth preferred embodiment of a multi-piece flexible chain implant, shown in an insertion position;

FIG. 7B is an exploded, side perspective view of the implant show in FIG. 7A;

FIG. 8A is a side perspective view of a seventh preferred embodiment of a multi-piece flexible chain implant, shown in an insertion position;

FIG. 8B is an exploded, side perspective view of the implant show in FIG. 8A;

FIG. 9 is a side perspective view of a prior art implant;

FIG. 10A is a side elevational view of an eighth preferred embodiment of a flexible chain implant, shown in an extended position;

FIG. 10B is a side elevational view of a ninth preferred embodiment of a flexible chain implant, shown in an extended position;

FIG. 11A is a side perspective view of a tenth preferred embodiment of a flexible chain implant, shown in an extended position;

FIG. 11B is an alternate, side perspective view of the flexible chain implant shown in FIG. 11A, also shown in an extended position;

FIG. 11C is another side perspective view of the flexible chain implant shown in FIG. 11A bending in a plane;

DESCRIPTION OF EMBODIMENTS

Figure 12A:
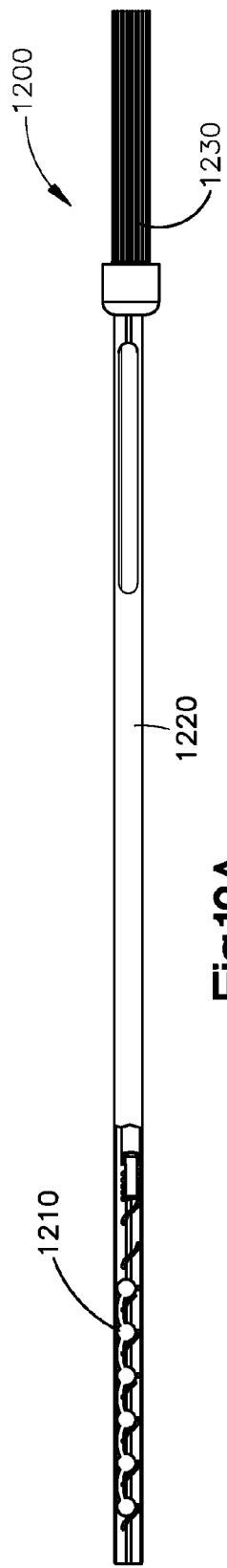
FIGS. 12A-12F depict various views of a cannula having an advancing mechanism for inserting a flexible chain implant into the interior volume of a vertebral body.
Figure 12B:
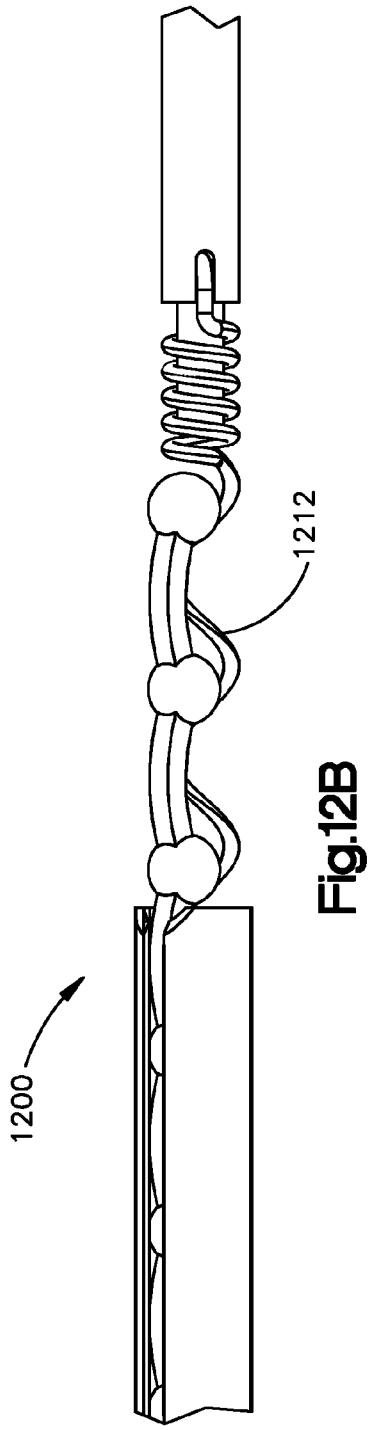

Certain terminology is used in the following description for convenience only and is not limiting. The words "right", "left", "lower", "upper", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body or with respect to the implant of the present application to which reference is made and are not meant to be limiting. The terminology includes the above-listed words, derivatives thereof and words of similar import.

Certain exemplary embodiments will now be described with reference to the drawings. In general, such embodiments relate to a vertebral augmentation system for aiding and/or augmenting a patient's spine. As generally understood by one of ordinary skill in the art, it should be understood that while the preferred vertebral augmentation system will be described as and may generally be used in the spine (for example, in the lumbar, thoracic or cervical regions), those skilled in the art will appreciate that the vertebral augmentation system may be used for aiding and/or augmentation other parts of the body such as, for example, joints, long bones or bones in the hand, face, feet, extremities, cranium, or in nearly any bone in the human body.

Referring to FIGS. 1-13B, a preferred vertebral augmentation system or flexible chain implant of the present application is directed to an implant and to a system and method for inserting the implant into a targeted vertebral body 602 of a vertebra 600, such as, for example, one which has been subjected to a VCF. Generally, the implant is sized and configured to be inserted into an interior volume 604 of the targeted vertebral body 602. Preferably, once inserted into the interior volume 604 of the targeted vertebral body 602, the implant will separate, unwrap, or unravel from an insertion position to an implanted configuration wherein the implant randomly coils, twists, stacks and/or wraps onto itself so that the implant may generally augment the interior volume 604 of the targeted vertebral body 602. The implant preferably separates and/or coils in the implanted configuration. Preferably, the implant is inserted into the targeted vertebral body via a minimally invasive surgical technique, such as, for example, through one or more cannulas 606, as will be described in greater detail below.

A first preferred embodiment of the flexible chain implant 10 is generally shown in FIG. 1. The implant 10 may be formed from a monolithic strip of material 12. That is, the implant 10 may be formed from a single, integral strip of material 12. The strip of material 12, and hence the implant 10, is preferably formed of bone, e.g., cortical bone, cancellous bone or both, but more preferably cortical bone. Thus, the implant 10 may be formed by cutting and/or machining a single, integral strip of material 12 from a piece of stock bone.

The strip of material 12 preferably includes a flexible section 14, which may be located generally in the middle of the strip of material 12, so that the strip of material 12 may be folded over onto itself. In this manner, as shown, the implant 10 includes a top member 20 and a bottom member 30 integrally connected at a coupled portion 50. The implant 10 may also include a gap 52 proximate the coupled portion 50. The gap 52 facilitates the separation of the top member 20 from the bottom member 30, for example once the implant 10 has been inserted into the interior volume 604 of the targeted vertebral body 602, as will be described in greater detail below. The gap 52 may also facilitate bending and/or folding of the top and bottom members 20, 30 relative to each other. When harvested or initially machined from stock bone, the flexible section 14 is generally not flexible, but is further processed, typically through demineralization, to make the flexible section 14 generally flexible, as will be described in greater detail below.

Figure 13A:
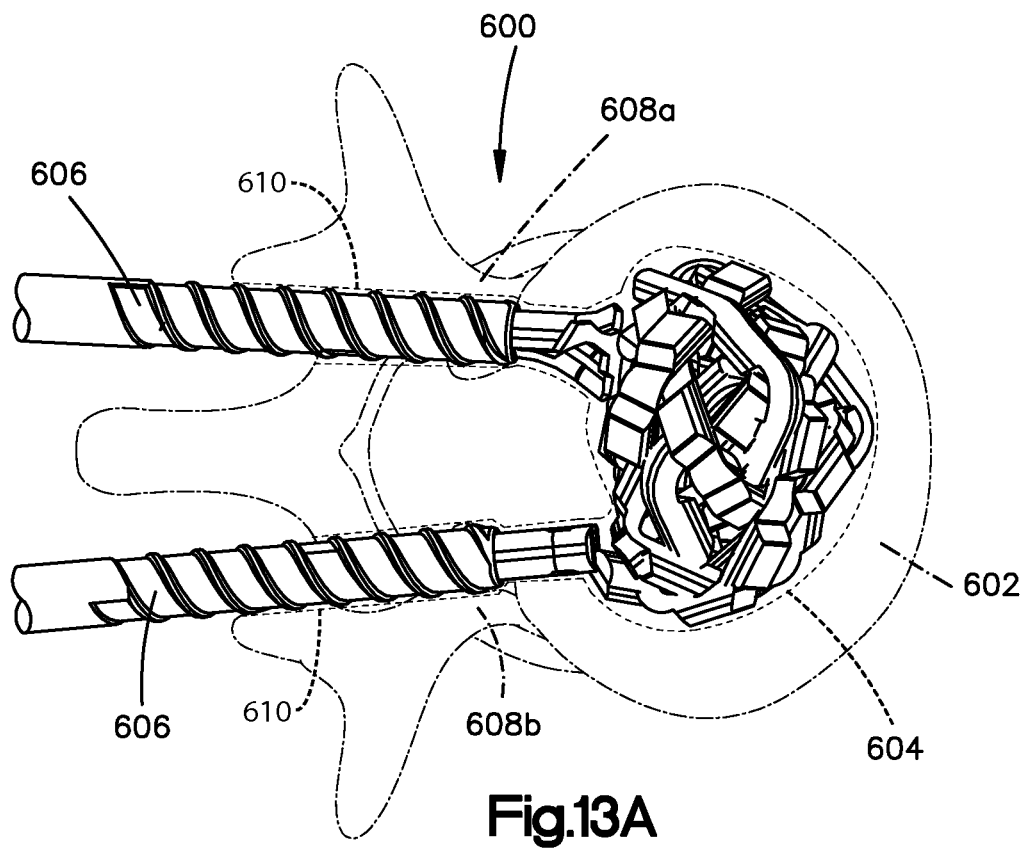
FIG. 13A is a top plan view of at least one of the flexible chain implants of the second, third, fourth, fifth or sixth preferred embodiments in an implanted configuration within a vertebral body of a vertebra.
Figure 13B:
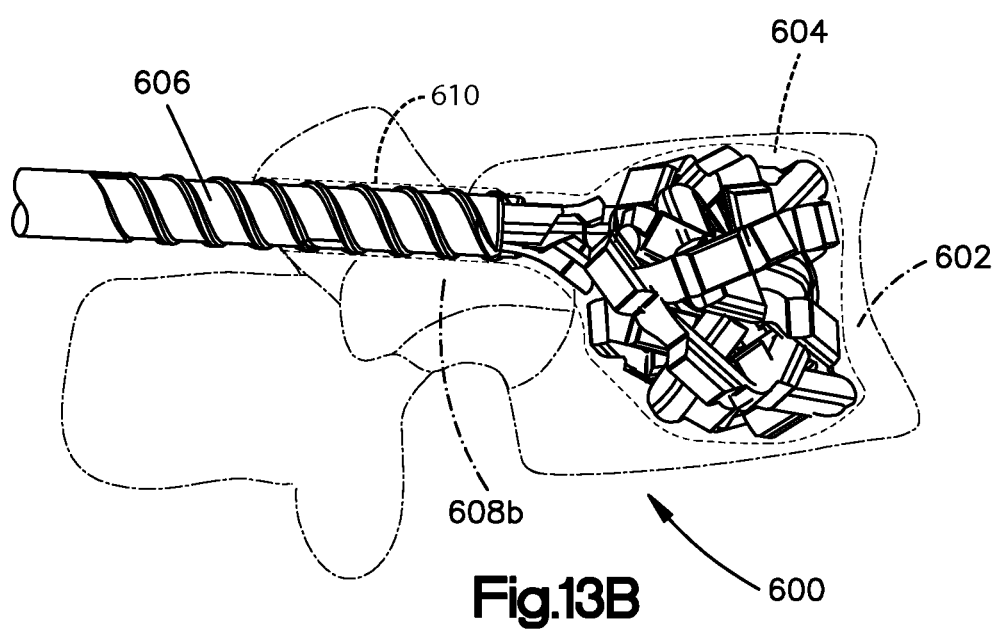
FIG. 13B is a side elevational view of at least one of the flexible chain implants of the second, third, fourth, fifth or sixth preferred embodiments in an implanted configuration within a vertebral body of a vertebra.

Referring to FIGS. 1, 13A and 13B, in use, the implant 10 is preferably inserted into the interior volume 604 of the targeted vertebral body 602 through a minimally invasive surgical technique, such as, for example, via one or more cannulas 606 while the implant is positioned in the insertion position. Once the implant 10 has been inserted or as the implant 10 moves out of the cannula 606 into the interior volume 604 of the targeted vertebral body 602, the top and bottom members 20, 30 preferably separate or unwrap from their insertion position and, generally, randomly coil and wrap or twist around themselves in the implanted configuration to substantially augment the interior volume 604. Preferably, in use, the non-integral, uncoupled or terminal end 54 of the implant 10 is inserted first into the cannula 606 and enters the interior volume 604 prior to the remainder of the implant 10. Although as will generally be appreciated by one of ordinary skill in the art, the coupled portion 50 of the implant 10 may be inserted first into the cannula 606. For example, the implant 10 of the first preferred embodiment may be pushed into the cannula 606 with the coupled portion 50 entering first, using a rod 80, as will be described in greater detail below.

The implant 10 may also be pulled into the interior volume 604 of the targeted vertebral body 602 through a first access, such as through a hole in a first or second pedicle 608a, 608b via, for example, a second access hole or channel formed in the opposing one of the first or second pedicle 608a, 608b. To facilitate pulling or pushing of the implant 10 into the interior volume 604 of the targeted vertebral body 602, the implant 10 may include a longitudinal channel or groove 70 (as best shown in FIG. 1) formed in the outer surface of the implant 10. The channel 70 preferably extends along the length of the implant 10 from the coupled portion 50 to the terminal end 54 in the insertion position. As shown, the channel 70 may be formed in a side of the implant 10. However, as will be generally appreciated by one of ordinary skill in the art, the channel 70 may be formed in any surface of the implant 10 including, but not limited to, the top or bottom surface. Alternatively, the implant 10 may include a longitudinal access hole or lumen (not shown) substantially parallel to the longitudinal axis of the implant 10 for receiving a rod for pulling the implant 10 into the interior volume 604 of the targeted vertebral body 602.

Referring to FIGS. 4A, 5A, 6A, 7A and 8A, the flexible chain implants 100, 200, 300, 400, 500 third, fourth, fifth, sixth and seventh preferred embodiments include a sloped or tapered surface at the terminal end 54 in the insertion position that slopes outwardly from a separation line between the top and bottom members 20, 30, generally away from the coupled portion 50. The sloped surface promotes separation of the top and bottom members 20, 30 from the insertion position to the implanted configuration as the implant 100, 200, 300, 400, 500 is inserted into the interior volume 604. In addition, the nodules 41 include tapered or sloping surfaces extending toward the hinges 43 that promote the unwinding of the top and bottom members 20, 30 relative to each other as the implant 100, 200, 300, 400, 500 is urged into the interior volume 604. The flexible chain implant 100, 200, 300, 400, 500 is not limited to inclusion of these tapered and/or sloping features and may function without these features. In addition, the tapered and sloping features may be included in any of the preferred embodiments of the present invention, despite whether the features are shown in the drawings of any of the particular embodiments.

The channel 70 is preferably sized and configured to receive a rod 80, which may be flexible or generally stiff. In accordance with the first preferred embodiment, the rod 80 includes an elongated portion 82 having a generally cylindrical shape and a bent portion 84. The bent portion 84 is preferably located adjacent an end of the elongated portion 82. The elongated portion 82 of the rod 80 is preferably sized and configured to be received, at least partially, within the channel 70 formed in the implant 10, while the bent portion 84 is preferably sized and configured to be received within the gap 52 formed in the implant 10. In this manner, both the implant 10 and the rod 80 may be received within the cannula 606. The rod 70 preferably is coupled to the implant 10 adjacent to the coupled portion 50 so that the user may pull or push the implant 10 through the cannula 606 and into the interior volume 604 of the targeted vertebral body 602. That is, the rod 70 preferably assists the user to pull or push the implant 10 through the cannula 606 and into the targeted vertebral body 602. After the implant 10 is inserted into the patient's body, the rod 70 may be removed. Specifically, once the implant 10 is positioned completely within the interior volume 604 and is out of the cannula 606, removal of the rod 80 from the interior volume 604 may promote the separating, unwrapping, uncoiling or unfolding of the implant 10 from the insertion position (FIG. 1) to the implanted configuration (e.g. FIGS. 13A and 13B). The rod 80 is preferably, generally rigid when configured to push the implant 10 into the interior volume 604 and is preferably, generally flexible or elastic when configured to pull the implant 10 into the interior volume 604, as will be understood by one having ordinary skill in the art.

In the first preferred embodiment, the top and bottom members 20, 30 of the implant 10 includes a plurality of cuts 25 formed in the outer surface thereof in order to increase the overall flexibility of the implant 10. Specifically, when the implant 10 of the first preferred embodiment is constructed of bone, the cuts 25 provide narrowed cross-sections along the length of the top and bottom members 20, 30, which may be subsequently demineralized to enhance flexibility, as will be described in greater detail below. That is, the cuts 25 define a plurality of alternating nodules 41, which are generally comprised of the relatively thick areas between the cuts 25 of the top and bottom members 20, 30, and hinges 43, which are generally comprised of portions of material at the cuts 25 of the top and bottom members 20, 30. The hinges 43 are preferably demineralized to the point at which they become flexible, at which point there is no or limited minerals left. However, the hinges 43 are not limited to being demineralized through their entire thickness and may be demineralized to nearly any depth that provides flexibility to the hinges 43 when the implant 10 is constructed of bone. In one exemplary embodiment, the implant 10 was constructed to have an overall length $L_1$ of about 108 mm (about 54 mm when folded) and was sized to fit within a cannula having an inner diameter of about 4.3 mm. The nodules 41 had a length $l_1$ of about 3.9 mm, a width $w_1$ of about 3.4 mm, and a height $h_1$ of about 2.0 mm. In comparison, the hinges 43 had a length $l_2$ of about 0.6 mm, a width $w_2$ of about 3.4 mm, and a height $h_2$ of about 1.0 mm. In the insertion position, the flexible chain implant 10 of the first preferred embodiment has a diameter D1 of approximately 4.0 mm, resulting in a clearance of approximately 0.3 mm when the implant 10 is located in the 4.3 mm preferred cannula 606. However, as will be appreciated by one of ordinary skill in the art, the size of the cannula 606, implant 10, nodules 41 and hinges 43 can be varied to suit the needs of the individual patients. Accordingly, the implants of the present invention are not limited to any particular dimensions.

Referring to FIGS. 2A-3B, 13A and 13B, a second preferred embodiment of a flexible chain implant 10' includes a plurality of alternating projections and recesses 40, 45 formed along an inner surface of the implant 10' so that when the strip of material 12 is folded over onto itself, the projections 40 formed in the top member 20 are received within the recesses 45 formed in the bottom member 30 and the projections 40 formed in the bottom member 30 are received within the recesses 45 formed in the top member 20 in the insertion position. In this manner, the top and bottom members 20, 30 may be nested together to minimize the size of the implant 10 in the insertion position (FIG. 2A) such that the implant 10' is slidably receivable within the cannula 606. The implant 10' may then be pulled or pushed through the cannula 606 and into the interior volume 604 of the targeted vertebral body 602 via, for example, a push rod (not shown) or the rod 80.

The implant 10' of the second preferred embodiment enables, depending on the stock material 13, may enable multiple strips of material 12a, 12b to be simultaneously machined from a single, monolithic piece of stock bone 13. That is, as generally depicted in FIGS. 3A and 3B, since nesting of the top and bottom members 20, 30 preferably includes alternating projections and recesses 40, 45, two strip of materials 12a, 12b may be simultaneously machined from a single piece of stock bone 13. Moreover, as will be described in greater detail below, during insertion of the implant 10' into the interior volume 604 of the targeted vertebral body 602, the implant 10' may be subjected to relatively large compressive stresses as the implant 10' is forced into the interior volume 604. As a result of these relatively large compressive stresses, the implant 10' may become damaged. However, as a result of nesting, the top and bottom members 20, 30, in effect, form a solid implant body that is capable of more readily withstanding the compressive forces. Thus, nesting generally minimizes the possibility that the implant 10' will be damaged during insertion.

Although FIGS. 3A and 3B depict completely separating the two strip of materials 12a, 12b from the stock bone 13, the implants 10, 10' of the first and second preferred embodiments may be cut or machined from the bone 13, generally in the inserted position (FIGS. 1 and 2A) without completely separating the two strip of material 12a, 12b during the original harvesting or machining process.

Alternatively, rather than being manufactured from a single, integral or monolithic strip of material 12, the top and bottom members 20, 30 may be formed from two or more strips of materials 12a, 12b, which are then coupled together, for example, at the coupled portion 50. The strips of materials 12a, 12b may be machined or harvested from a single bone 13, from multiple bones or from nearly any other material that is able to take on the general shape and size of the strip of material 12a, 12b and withstand the normal operating conditions of the implant 10, 10'. Constructing a multiple-piece flexible chain implant (FIGS. 4A-8B) may be particularly useful in situations where one is not able to obtain a single strip of material 12 of sufficient size to produce an integrally formed implant 10, 10'. The top and bottom members 20, 30 may be coupled by any means now or hereafter known.

Referring to FIGS. 4A and 4B, in a third preferred embodiment, a flexible chain implant 100 includes the top and bottom members 20, 30 formed with the alternating projections 40 and recesses 45, a dovetail-shaped projection 42 and a dovetail-shaped recess 47 at the coupled portion 50. As shown, the top and bottom members 20, 30 are coupled together by interconnecting the dovetail-shaped projection 42 and the dovetail-shaped recess 47 such that when the top member 20 and the bottom member 30 are separated or unwrapped from each other, such as, in direction A, the dovetail shaped projection 42 and recess 45 remain interconnected and secure the top member 20 to the bottom member 30. The implant 100 may also include one or more pins (not shown) extending proximate or through the dovetail-shaped projection 42 and recess 47 for further securing the top and bottom members 20, 30. As shown, the implant 100 of the third preferred embodiment includes a single pair of dovetail-shaped interconnecting projections 42 and recesses 47. More preferably, the dovetail-shaped projection 42 and recess 47 are formed adjacent the coupled portion 50 of the implant 100 so that, similar to the integral implant 10' of the second preferred embodiment, the projections 40 formed in the top member 20 may be received within the recesses 45 formed in the bottom member 30 and the projections 40 formed in the bottom member 30 may be received within the recesses 45 formed in the top member 20 so that the implant 100 of the third preferred embodiment may be nested together in the insertion position. Once inserted, however, the top and bottom members 20, 30 may separate or unwrap from their insertion position and, generally, randomly coil and wrap or twist around itself to augment the interior volume 604 of the targeted vertebral body 602 in the implanted configuration. The dovetail-shaped projection 42 and recess 47 preferably, fixedly secure the top member 20 to the bottom member 30 at the coupled portion 50 of the implant 100 even after the implant 100 has been inserted into the interior volume 604. In this manner, the dovetail-shaped projection 42 and recess 47 operate in a manner substantially similar to the integral coupled portion 50 formed from the monolithic portion of bone or other material of the implant 10' of the second preferred embodiment. However, the coupled portion 50 is not limited to fixedly securing the top and bottom members 20, 30 together in the implanted configuration and may separate once the implant 100 is inserted into the interior volume 604.

Alternatively and/or in addition, the top and bottom members 20, 30 may be coupled together by demineralizing the implant 100 of the third preferred embodiment. That is, by demineralizing the top and bottom members 20, 30, the top and bottom members 20, 30 may become fixed relative to each other at the coupled portion 50 of the implant 100 of the third preferred embodiment. Thus, demineralizing the top and bottom members 20, 30, welds or otherwise secures the members 20, 30 together when the members 20, 30 are demineralized with the dovetail-shaped projection 42 and recess 47 engaged with each other. Demineralizing the implant 100 may be particularly useful in combination with a corresponding dovetail joint as traditionally dovetailed, multi-piece allograft implants have incorporated a pin to further secure the pieces together. Demineralizing the implant 100 may eliminate the requirement for any additional pin, thereby reducing part count and generally simplifying the construction of the implant 100. In such a demineralization process, the inner surfaces of the top and bottom members 20, 30 are masked or otherwise separated to space the inner surfaces from each other to provide exposure to the demineralizing medium and to generally prevent these inner surfaces from welding or becoming fixed to each other during demineralization. The coupled portion 50 of the implant 100 is not limited to being constructed of the described demineralized dovetail-type joint and may be constructed of nearly any two allograft surfaces positioned in facing engagement or close proximity to each other and demineralized and/or pinning, press fitting, capping or other known fastening mechanisms and methods that would be apparent to one having ordinary skill in the art.

In order to demineralize the top and bottom members 20, 30 such that they are welded or fixed together, the implant 100, etc. may be demineralized in a bath of HCl concentration for several hours to provide a desired penetration percentage into the thickness of the top and bottom members 20, 30 thus resulting in a relatively deep demineralized layer. The duration of demineralization is about fifteen minutes to about eight hours, and preferably between about 1.5 hours to about 2 hours. The HCl concentration is between about 0.5 HCl to about 2.5 HCl, and preferably between about 0.6 HCl and about 1.0 HCl. Although as will be generally appreciated by one of ordinary skill in the art, the duration of dimeralization and the HCl concentration may be adjusted in order to obtain the desired levels of flexibility, to retain some rigidity in the nodules, and to obtain welding of the multi-piece implants. The implants of the present invention are not limited to any particular duration of demineralization and/or HCl concentration. When incorporating alternating projections 40 and recesses 45, the plurality of nodules 41 generally are comprised of the relatively thick projections 40 while the hinges 43 generally are comprised of the portions of material at the recesses 45. The penetration percent of demineralization, for nodules 41 of the top and bottom members 20, 30 is about one-half millimeter (0.5 mm) of demineralization on all sides. Hinges 43 are preferably demineralized to the point at which they become flexible, at which point there is no or limited minerals left. However, the hinges 43 are not limited to being demineralized through their entire thickness and may be demineralized to nearly any depth that provides flexibility to the hinges 43 when the implant 10', 100, etc. are constructed of bone. It should be noted that the method of forming an implant from coupled bone using demineralization to fixedly secure the various components or members of the implant is not limited to the implants described herein and may be used to couple any multi-piece implant formed from bone now or hereafter known in the art.

In exemplary second, third, fourth, fifth, sixth and seventh preferred embodiments, the top and bottom members 20, 30 of the implant 10', 100, etc. were constructed to have an overall length $L_3$ of about 40 mm to about 52 mm and was sized to fit within a cannula 606 having an inner diameter of about 4.3 mm. The nodules 41 had a length $l_3$ of about 3.9 mm to about 6.7 mm, a width $w_3$ of about 3.6 mm to about 3.8 mm, and a height $h_3$ of about 2.5 mm to about 3.1 mm. In the insertion position, the implants 10', 100, etc. of the second, third, fourth, fifth, sixth and seventh preferred embodiments have a diameter $D_3$ of approximately 3.5 mm to approximately 4.0 mm. In addition, the hinges 43 preferably have a length $l_4$ of about 3.1 mm to about 4.1 mm, a width $w_4$ of about 3.3 mm to about 3.6 mm, and a height $h_4$ of about 0.5 mm to about 1.0 mm. Although as will be generally appreciated by one of ordinary skill in the art, the size of the implants 10', 100, etc., nodules 41 and hinges 43 can be varied to suit the needs of the individual patients. The implants of the present invention are not limited to any particular dimensions.

To ensure that the inner surfaces of the top and bottom members 20, 30 of the implant 100 of the third preferred embodiment remain separatable once inserted into the interior volume 604, preferably only a portion of the top and bottom members 20, 30 are placed into contact with one another during a majority of the demineralization. The remaining inner surfaces of the top and bottom members 20, 30 are separated from one another during demineralization to limit the possibility that they do not become welded, secured or fixed together. For example, a wedge, masking or a barrier may be inserted between the inner surfaces of the top and bottom members 20, 30 and, in particular, between the alternating projections 40 and recesses 45 formed in the top and bottom members 20, 30, to create a space between the top and bottom members 20, 30 to limit the possibility that they do not become welded, secured or fixed together during demineralization.

Referring to FIGS. 5A-5C, a flexible chain implant 200 in accordance with a fourth preferred embodiment includes a cap 240 to couple the top and bottom members 20, 30 together. The top and bottom members 20, 30 of the fourth preferred embodiment include a projection 256 comprised of a top projection 256a and a bottom projection 256b at the coupled portion 50 thereof when the top and bottom members 20, 30 are nested together. That is, as shown, the top member 20 includes the top projection 256a and the bottom member 30 includes the bottom projection 256b such that when the top and bottom members 20, 30 are nested together, the projection 256 is formed. The cap 240 preferably includes a recess 242 sized and configured to receive the projection 256 at the coupled portion 50 of the top and bottom members 20, 30. Moreover, as will be generally appreciated by one of ordinary skill in the art, the cap 240 may be configured to couple the top and bottom members 20, 30 at another location.

In use, the cap 240 is constructed and arranged to retain the coupled portion 50 of the top and bottom members 20, 30 together so that the cap 240 fixedly secures the top member 20 to the bottom member 30 at the coupled portion 50 of the implant 200 even after the implant 200 has been inserted into the interior volume 604 of the targeted vertebral body 602. However, the coupled portion 50 is not limited to fixedly securing the top and bottom members 20, 30 together in the implanted configuration and may separate once the implant 200 is inserted into the interior volume 604. By way of non-limiting example, the recess 242 formed in the cap 240 and the projection 256 formed at the coupled portion 50 of the nested top and bottom members 20, 30 may be in the form a dovetailed joint. Alternatively, as will be generally appreciated by one of ordinary skill in the art, the cap 240 may include the projection 256 and the implant 200 may be formed with the recess 242. When the cap 240, top member 20 and bottom member 30 are constructed of the preferred bone material, the coupled portion 50 may be demineralized to secure or fix the cap 240 and projection 256 together at the coupled portion 50.

Referring to FIGS. 6A and 6B, the top and bottom members 20, 30 of a flexible chain implant 300 in accordance with a fifth preferred embodiment includes a top end piece 322 and a bottom end piece 332, respectively, having top and bottom apertures 324, 334, respectively. As shown, the top and bottom end pieces 322, 332 are preferably located adjacent to the coupled portion 50 of the implant 300 but need not be located at the extreme end of the top and bottom members 20, 30 in the insertion position. The top and bottom apertures 324, 334 formed in the top and bottom end pieces 322, 332 are sized and configured to receive a pin 360. During assembly, the top end piece 322 and the bottom end piece 332 are preferably aligned such that the top aperture 324 and the bottom aperture 334 are aligned so that the top and bottom apertures 324, 334 receive the pin 360 to secure and retain the top and bottom members 20, 30 together. In use, the top and bottom end pieces 322, 332 are constructed and arranged to retain the coupled portion 50 of the top and bottom members 20, 30 together so that the pin 360 and top and bottom end pieces 322, 332 fixedly secure the top member 20 to the bottom member 30 at the coupled portion 50 of the implant 300 even after the implant 300 has been inserted into the interior volume of the targeted vertebral body 602. However, the coupled portion 50 is not limited to fixedly securing the top and bottom members 20, 30 together in the implanted configuration and may separate once the implant 300 is inserted into the interior volume 604.

One of the top and bottom members 20, 30 (shown as the top member 20) may also include a stopper projection 326. As shown, the stopper projection 326 is preferably formed in one or as part of one of the projections 40 formed on the implant 300. In use, the stopper projection 326 acts as a physical barrier to prevent inadvertent removal of the pin 360, particularly in the insertion position. Moreover, the stopper projection 326 may be sized and configured to surround the head 362 of the pin 360 to limit exposure of the pin 360. For example, as shown, the stopper projection 326 may include a recess 328 for receiving the head 362 of the pin 360.

Referring to FIGS. 7A and 7B, a flexible chain implant 400 in accordance with a sixth preferred embodiment includes a longitudinal extending projection 422 formed in the top member 20 adjacent to the coupled portion 50 while the bottom member 30 includes an end piece 432 having a corresponding longitudinal channel 434 for receiving the longitudinal extending projection 422. The longitudinal extending projection 422 and the end piece 432 are preferably located adjacent to the coupled portion 50 of the implant 400 but need not be located at the extreme end of the top and bottom members 20, 30 in the insertion position. Preferably, the longitudinal extending projection 422 is constructed and arranged for snap-fitting into the corresponding longitudinal channel 434 formed in the end piece 432 of the bottom member 30. Once inserted, the longitudinal channel 434 is preferably constructed and arranged to retain the longitudinal extending projection 422 and hence limit separation of the top and bottom members 20, 30 at the coupled portion 50.

In use, the longitudinal projection 422 and channel 434 are constructed and arranged to retain the coupled portion 50 of the top and bottom members 20, 30 together so that the longitudinal projection 422 and channel 434 fixedly secure the top member 20 to the bottom member 30 at the coupled portion 50 of the implant 400 even after the implant 400 has been inserted into the interior volume 604 of the targeted vertebral body 602. However, the coupled portion 50 is not limited to fixedly securing the top and bottom members 20, 30 together in the implanted configuration and may separate once the implant 400 is inserted into the interior volume 604. Alternatively, as will be generally appreciated by one of ordinary skill in the art, the bottom member 30 may include the longitudinal projection 422 and the top member 20 may include the end piece 432 and longitudinal channel 434. When the top member 20 and bottom member 30 including the longitudinal projection 422 and channel 434 are constructed of the preferred bone material, the coupled portion 50 may be demineralized to further secure or fix the projection 422 and channel 434 together at the coupled portion 50.

Referring to FIGS. 8A and 8B, a flexible chain implant 500 in accordance with a seventh preferred embodiment includes a longitudinal extending projection 522 formed in the top member 20 adjacent to the coupled portion 50 of the implant 500 while the bottom member 30 includes an end piece 532 having a corresponding longitudinal channel 534 for receiving the longitudinal extending projection 522 formed on the top member 20. The longitudinal extending projection 522 and the end piece 532 are preferably located adjacent to the coupled portion 50 of the implant 500 but need not be located at the extreme end of the top and bottom members 20, 30 in the insertion position. Preferably, the longitudinal extending projection 522 is slideable into engagement with the corresponding longitudinal channel 534 formed in the end piece 532 on the bottom member 30. Once inserted, the longitudinal channel 534 is preferably constructed and arranged to retain the longitudinal extending projection 522 and hence limit separation of the top and bottom members 20, 30 at the coupled portion 50.

In use, the longitudinal extending projection 522 and channel 534 are constructed and arranged to retain the coupled portion 50 of the top and bottom members 20, 30 together so that the longitudinal extending projection 522 and channel 534 fixedly secure the top member 20 to the bottom member 30 at the coupled portion 50 of the implant 500 even after the implant 500 has been inserted into the interior volume 604 of the targeted vertebral body 602. However, the coupled portion 50 is not limited to fixedly securing the top and bottom members 20, 30 together in the implanted configuration and may separate once the implant 500 is inserted into the interior volume 604. Alternatively, as will be generally appreciated by one of ordinary skill in the art, the bottom member 30 may include the longitudinal extending projection 522 and the top member 20 may include the end piece 532 and the longitudinal channel 534. When the top member 20 and bottom member 30 including the longitudinal extending projection 522 and channel 534 are constructed of the preferred bone material, the coupled portion 50 may be demineralized to further secure or fix the projection 522 and channel 534 together at the coupled portion 50.

As previously stated, the flexible chain implants 10, 10', 100, 200, 300, 400, 500 of the preferred embodiments are constructed of bone. Alternatively, as will be described in greater detail below, the preferred implants 10, 10', 100, 200, 300, 400, 500 may be constructed of any biocompatible material now or hereafter known having the desired characteristics including, but not limited to, synthetic material, a biocompatible polymer, metal, ceramic, composite or any combination thereof. The preferred implants 10, 10', 100, 200, 300, 400, 500 may be absorbable or resorbable by the body and for specific applications may have osteoinductive properties or be made at least partly from osteoinductive materials. Accordingly, the preferred flexible chain implants 10, 10', 100, 200, 300, 400, 500 may be constructed of nearly any material or combination of materials that is able to take on the general shape and size and withstand or adapt to the normal operating conditions of the implants 10, 10', 100, 200, 300, 400, 500.

An exemplary method for fabricating a preferred flexible chain implant 10, 10', 100, 200, 300, 400, 500 from bone will now be described. In this example, a piece of stock allograft femoral bone, potentially the bone 13 shown in FIGS. 3A and 3B, is used as a base material, preferably, cortical allograft bone. Other bones may be used including, but not limited to, radius, humorous, tibia, femur, fibula, ulna, ribs, pelvic, vertebrae, etc.

The selected bone 13 is preferably roughly machined to the desired general shape of the implant and/or components of the implant from the stock allograft bone 13. For example, conventional milling, sawing, grinding and/or other fabrication techniques may be used. After machining the desired general shape, the implant and/or components of the implant are removed and/or separated from the raw material of bone 13 and excess material is removed. Additional machining is performed as necessary to remove any additional excess material and to form the desired shape and configuration of the implant and/or components of the implant. The shaped implant may be coupled and/or demineralized as necessary. The component portions of the implant are mounted together (see FIGS. 4A-8B) and the preferred monolithic implants 10, 10' or preferred, assembled multi-piece implants 100, 200, 300, 400, 500 are subjected to demineralization. The implants 10, 10', 100, 200, 300, 400, 500 are preferably demineralized until the hinges 43 are flexible enough to permit the implants 10, 10', 100, 200, 300, 400, 500 to move to and between the insertion position and the implanted configuration, such that the nodules 41 maintain general rigidity, at least at their core, and until the coupled portion 50 secure the top and bottom members 20, 30 of the multi-piece implants 100, 200, 300, 400, 500. The amount of time and/or the concentration or composition of the demineralizing solution may be varied to provide the desired amount of flexibility, elasticity, or to weld, secure or fix a portion of the top and bottom members 20, 30 together. Demineralization may be applied to specific portions of the preferred implants 10, 10', 100, 200, 300, 400, 500, for example, masking or shielding the portions that do not or should not be treated. For example, by masking portions intended to remain non-flexible, the remaining portions of the implants 10, 10', 100, 200, 300, 400, 500 may be partially or entirely demineralized, and the non-flexible portions may retain their original mineralized state prior to the masking.

Various other configurations and methods for manufacturing monolithic, multi-piece or other coupled implants may be used. The choice of methods may depend, at least in part, on the material or materials to be used in the particular implant. For example, if the implant is made of a biocompatible polymeric material, the implant may be manufactured by using conventional manufacturing methods such as but not limited to milling and turning. Alternatively, if the implant is made out of a biocompatible polymeric material, the entire implant may be injection molded. If the implant is constructed of a metallic material, it may be manufactured using conventional manufacturing methods such as but not limited to milling and turning. However, the flexible components may undergo secondary processes such as annealing. The secondary process may be limited to the flexible portions of the implant, for example by masking or shielding the non-flexible portions.

Referring to FIGS. 10A and 10B, a flexible chain implant 1000', in accordance with eighth and ninth preferred embodiments, includes a plurality of bodies 1010 and a plurality of linking portions 1020 wherein each of the plurality of bodies 1010 includes a plurality of facets 1030. The plurality of bodies 1010 includes a plurality of facets 1030 having or forming a hexagon shape in the eighth preferred embodiment and forming a pentagon shape in the ninth preferred embodiment. Alternatively, the plurality of bodies 1010 may include a plurality of facets 1030 having or forming a polyhedral shape. It is to be understood that the shape of the plurality of bodies 1010 may be varied without deviating from the scope of the invention so long as the plurality of bodies 1010 are formed with a plurality of facets 1030 defining substantially flat surfaces.

Forming each of the plurality of bodies 1010 with a plurality of facets 1030 facilitates stacking of the plurality of bodies 1010 in the implanted configuration. That is, a facet 1030 formed on one body 1010 may contact and come into facing engagement with a facet 1030 formed on another, adjacent body 1010 and reduce the amount of space present between two bodies 1010 as compared to other shapes, such as circular bodies, which tend to result in point contacts between the facing bodies in the implanted configuration. Moreover, because the implant 1000' may bend, wrap, coil, etc., when inserted into the interior volume 604 of the targeted vertebral body 602, non-adjacent bodies 1010 may also contact one another. Therefore, the reduction in gaps between the contacting bodies 1010 provided by forming the plurality of bodies 1010 with a plurality of facets 1030 may provide an increased density of bodies 1010 within the interior volume 604 of the targeted vertebral body 602.

Furthermore, forming the plurality of bodies 1010 with a plurality of facets 1030 may facilitate inserting the implant 1000' into the interior volume 604 of the vertebral body 602. That is, as previously described above in connection with the implants 10, 10', 100, 200, 300, 400, 500 of the first through seventh preferred embodiments, generally, during insertion of the implant 1000' into the interior volume 604 of the targeted vertebral body 602, the implant 1000' may be subjected to relatively large compressive stresses as the implant 1000' is forced into the interior volume 604. The plurality of bodies 1010 with a plurality of facets 1030 contact one another when the implant 1000' is pushed into the interior volume 604 of the targeted vertebral body 602 via, for example, a cannula 606. By providing the plurality of facets 1030 which come into facing engagement during insertion, forces on the facets 1030 are distributed over the facet 1030 surfaces. Moreover, by increasing the surface area in which bodies 1010 contact each other, the force at which the implant 1000' may be inserted is increased.

In the eighth and ninth preferred embodiments, the plurality of bodies 1010 of the implant 1000' defines a longitudinal axis 1001 (e.g., a body axis) when the implant 1000' is oriented in an extended position (FIGS. 10A and 10B). The plurality of linking portions 1020 preferably define a longitudinal axis 1022 (e.g., a link axis) in the extended position. The link axis 1022 is preferably off-set or off-centered from the body axis 1001 in the extended position (as shown in FIGS. 10A and 10B). Specifically, in the eighth and ninth preferred embodiments of at least FIGS. 10A and 10B, the link axis 1022 is preferably located a distance A from the body axis 1001. By providing off-centered linking portions 1020, the implant 1000' may be partially restricted in its ability to bend in at least one plane, such as bending of the ends of the linking portions 1020 toward the opposite sides of the facets 1030, because the relatively rigid facets 1030 bump into each other and restrict such bending. Restricting the ability of the implants 1000' to bend in one plane enables the user to better control which way the implant 1000' starts to bend and/or coil within the interior volume 604 of the targeted vertebral body 602. However, as will be generally appreciated by one of ordinary skill in the art, the link axis 1022 may be coaxial with the body axis 1001. In addition, the linking portions 1020 may permit twisting and misalignment of the facets 1030 relative to the body axis 1001, thereby generally permitting bending and/or twisting of the individual facets 1030 relative to each other in nearly any direction.

Referring to FIGS. 11A-11C in a tenth preferred embodiment, a flexible chain implant 1100 includes the plurality of bodies 1110 having tapered or curved surfaces 1112 such that the plurality of tapered or curved bodies 1110 have a narrow width 1114 and a wider width 1116. Preferably, the plurality of linking portions 1120 interconnect the plurality of tapered bodies 1110 proximate the narrow width 1114. The tapered or curved surfaces 1112 further include an abutment surface 1118 such that adjacent tapered or curved bodies 1110 may contact one another proximate the wider width 116. The plurality of abutment surfaces 1118 define a longitudinal axis 1119 (e.g., an abutment axis) in an extended position (FIGS. 11A and 11B), wherein the abutment axis 1119 is off-set or off-centered from a body axis 1101 in the extended position (as shown in FIG. 11A). Specifically, in the tenth preferred embodiment, the abutment axis 1119 is preferably located a distance B from the body axis 1101 and off-set from a link axis 1122 in the extended position, as will be described in greater detail below. Preferably, the abutment axis 1119 is located on the opposite side of the longitudinal axis 1101 of the implant 1100 as compared to the link axis 1122.

During insertion of the implant 1100 into the interior volume 604 of the targeted vertebral body 602 via, for example, a cannula 606, the implant 1100 may be subjected to relatively large compressive stresses as the implant 1100 is pushed into the interior volume 604 of the targeted vertebral body 602. As a result of the plurality of bodies 1110 incorporating a tapered or curved surface 1112 which defines an abutment surface 1118, adjacent bodies 1110 may contact one another, in effect, forming a solid implant that is capable of withstanding the compressive forces. Moreover, the cannula 606 is preferably sized and configured to snuggly receive the implant 1100 therein so that the implant 1100 is braced by the inner surface of the cannula 606. The sizing and arrangement of the plurality of bodies 1110 and the linking portions 1120 directs the majority of compressive forces, during advancement of the implant 1100 through the cannula 606 and into the interior volume 604 of the targeted vertebral body 602, through the abutment surfaces 1118. Providing a plurality of abutment surfaces 1118 may also enhance tactical feedback as the implant 1100 is pushed through the cannula 606, as the implant 1100 generally feels like a solid implant to the technician conducting the procedure.

The plurality of linking portions 1120, which are thinner than the plurality of bodies 1110, may be located off-centered, e.g., a longitudinal axis 1122 of the linking portions 1120 is preferably located a distance C from the longitudinal axis 1101 of the implant 1100 in the extended position. By providing off-centered linking portions 1120, the implant 1100 may be restricted in its ability to bend in at least one plane. Restricting the implants 1100 ability to bend in one plane enables the user to better control which way the implant 1100 starts to bend and/or coil within the interior volume 604 of the targeted vertebral body 602. However, as will be generally appreciated by one of ordinary skill in the art, the longitudinal axis 1122 of the linking portions 1120 may be coaxial with the longitudinal axis 1101 of the implant 1100.

Referring to FIG. 11C, in the tenth preferred embodiment, the shape and configuration of the implant 1100 is configured for harvesting from a single, cylindrical section of bone, generally to improve the yield of the specific bone. Specifically, if a particular bone is not relatively long or does not include a relatively long portion to accommodate construction of the relatively long, flexible chain implants 10, 10', 100, 200, 300, 400, 500 and/or components of the first through seventh preferred embodiments, the implant 1100 of the tenth preferred embodiment may be rough machined in the generally cylindrical configuration, shown in FIG. 11C. The implant 1100 is then preferably subjected to demineralization such that the linking portions become flexible and the bodies 1110 maintain some rigidity. Following demineralization, the implant 1100 may be oriented in the expanded position and/or inserted in the cannula 606 in the insertion position. In addition, the implant 1100 may be urged through the cannula 606 into the interior volume 604 and fold, wind and generally, randomly position itself in the implanted configuration.

Referring to FIGS. 1A-13B, a minimally invasive method of augmenting a damaged vertebral body 602, e.g., following a VCF, may include inserting one or more of the preferred flexible chain implants 10, 10', 100, 200, 300, 400, 500, 1000', 1100 into the interior volume 604 of the targeted vertebral body 602 between the endplates of the vertebral body 602. One or more flexible chain implants 10, 10', 100, 200, 300, 400, 500, 1000', 1100 may be inserted as a preventive measure to augment the vertebral body 602 before compression or a compression fracture. For example, generally, a passageway 610 may be formed in the outer cortical shell of the targeted vertebral body 602 by a trocar, drill or other instrument. By way of non-limiting example, the passageway 610 may be formed into the interior of the vertebral body 604 through a posterior portion of the vertebral body, such as, for example, through a pedicle 608a, 608b. The cannula 606 may then be introduced into the interior volume 604 of the targeted vertebral body 602 through the passageway 610. The implant 10, 10', 100, 200, 300, 400, 500, 1000', 1100 is inserted into the interior volume 604 of the targeted vertebral body 602 through the cannula 606 and into interior volume 604. The implant 10, 10', 100, 200, 300, 400, 500, 1000', 1100 may be inserted into the interior volume 604 by, for example, a push rod. Utilization of the push rod is particularly useful for inserting the preferred implants 10, 10', 100, 200, 300, 400, 500, 1000', 1100, as the implants 10, 10', 100, 200, 300, 400, 500, 1000', 1100 are designed to withstand the relatively large compressive forces that may be experienced during insertion.

Figure 12C:
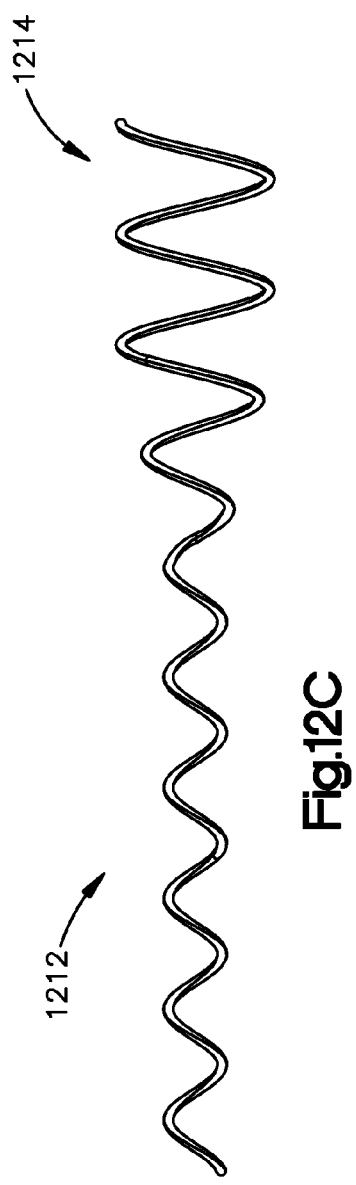

Alternatively, as shown in FIGS. 12A-12F, an exemplary embodiment of a cannula 1200 may incorporate an advancement mechanism 1210. As best shown in FIGS. 12A-12E, the advancement mechanism 1210 may be in the form of a corkscrew. The cork screw is preferably adapted for inserting the flexible chain implants 1000, 1000' and 1100 of the prior art and the eighth and ninth preferred embodiments. That is, the advancement mechanism 1210 may include a section of spiraling geometry 1212. The spiraling geometry 1212 includes an inner diameter, an outer diameter, a pitch, and a cross-sectional thickness and shape. The spiraling geometry 1212 resembles a spring (with a cross section that is circular, square, rectangular, etc.), an auger, a worm gear, or a screw. Using the spiraling geometry 1212, the implants 1000, 1000', 1100 could be fed or weaved into the individual coils or spirals of the spiraling geometry 1212 of the advancement mechanism 1210. As shown in FIG. 12C, the proximal end 1214 of the spiraling geometry 1212 may initially start at a larger diameter which may taper down to the functional diameter to facilitate loading of the implants 1000, 1000', 1100 into the advancement mechanism 1210. Loading may be done through an opening in the side of the cannula 1200 or the implants 1000, 1000', 1100 may be wound around the end of the advancement mechanism's spirals.

Figure 12D:
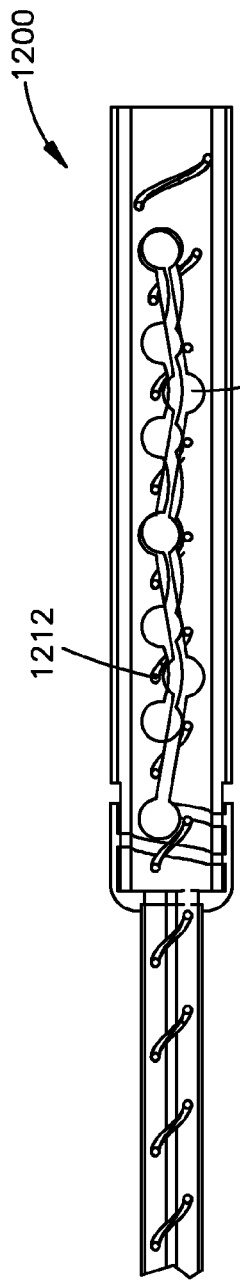
Figure 12E:
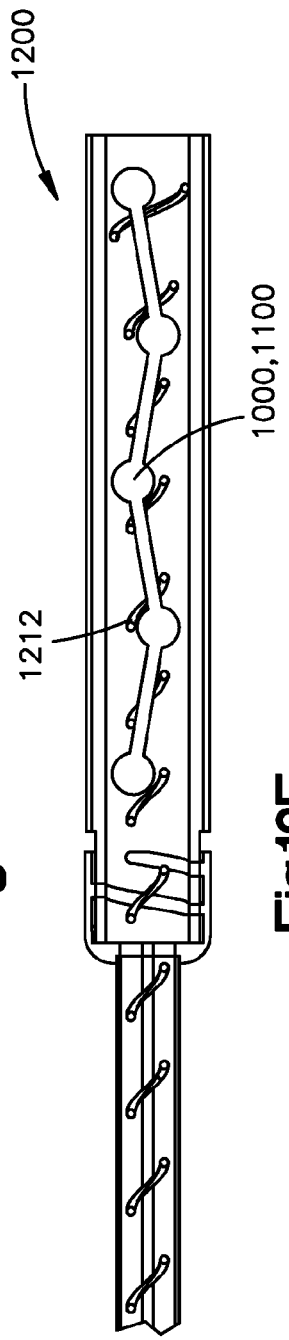

The spiraling geometry 1212 may be off-axis to the longitudinal axis of the implants 1000, 1000', 1100. Alternatively, as best shown in FIGS. 12D and 12E, the implants 1000, 1000', 1100 may have a longitudinal axis that is substantially coincident with the longitudinal axis of the spiraling geometry 1212 within the cannula 1200.

As best shown in FIG. 12A, the cannula 1200 may also include a handle 1230, which may be detachable to facilitate surgeon placement via hand or mallet impaction, and an optional extended section 1220 between the handle 1230 and the advancement mechanism 1210. The cannula 1200 may also include a locking mechanism to help prevent separation of the advancement mechanism 1210 from the cannula 1200. The locking mechanism preferably is capable of being disengaged as part of normal operation of the instrument and/or to facilitate sterilization. The cannula 1200 is also preferably sized and configured to permit the implants 1000, 1000', 1100 to travel down through the cannula 1200. Accordingly, the cannula 1200 is sized and configured to prevent the implants 1000, 1000', 1100 from rotating in place with the advancement mechanism 1210. For example, a mechanism for preventing the implants 1000, 1000', 1100 from rotating in place may be formed within the sidewall of the cannula 1200. For example, the inner sidewall of the cannula 1200 may include a longitudinal slot or track that is sized and configured to mate with at least a portion of the implants 1000, 1000', 1100. Alternatively, the cannula 1200 may have a non-circular-shaped lumen. For example, the cannula 1200 may have an oval shaped inner diameter which tightly matches the geometry of the implants 1000, 1000', 1100. This eliminates the necessary space needed to allow the implants 1000, 1000', 1100 to rotate in place.

Figure 12F:
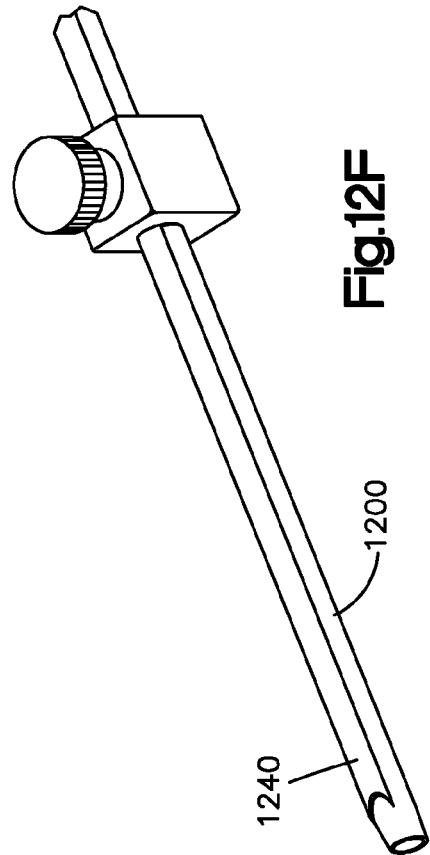

As best shown in FIG. 12F, the cannula 1200 may also include an adjustable skin stop attachment 1240 to help maintain the cannula 1200 at the desired depth within the vertebral body 602. A small venting shaft may also be used along the side of the cannula 1200 in order to vent any air that may get forced into the operating site. This could be especially important if the same cannula 1200 is used to inject liquid bone void filler. If the cannula 1200 is to be used to inject liquid bone void filler, a lure lock feature may be preferred on the cannula 1200 to connect it to the filler's injection device. In the event that a portal is included in the side of the cannula 1200 as an access point to couple the implants 1000, 1000', 1100 within the spiraling geometry 1212, a cap or door may be provided to snap on, hinge, or slide over the loading portal to help retain the coupling.

The implant is preferably inserted into the vertebral body 602 in an insertion position and is oriented in an implanted configuration in the vertebral body 602 so that the implant augments the interior volume 604 of the targeted vertebral body 602 so that large pockets or voids are limited within the interior volume 604, while small voids amenable to boney in-growth and providing a vascular pathway are provided. The implant preferably separates or unwraps from the insertion position and, generally, randomly coils and wraps or twists around itself in the implanted configuration.

Insertion of the implant into the interior volume 604 of the targeted vertebral body 602 may compact the cancellous and/or osteoporotic bone inside the vertebral body 602 and/or restore or support the vertebral body 602. Alternatively, after the passageway 610 is formed in the vertebral body 602, instruments such as, for example, curettes or a balloon catheter may be used to compress and compact the bone inside the vertebral body 602 to create the interior volume 604. The instruments may then be removed. Alternatively, the balloon portion of the catheter may remain within the vertebral body 602 or may form a container for the implant. The interior volume 604 in the vertebral body 602 also may be formed by removing bone material as opposed to compacting the bone. For example, a reamer or other apparatus could be used to remove bone material from the inside of the vertebral body 602. Further, the interior volume 604 may be formed by urging the implant into the body 602 to restore vertebral body height following a VCF.

Whether a cavity is first formed in the targeted vertebral body 602 or the implant is inserted without first creating a cavity, as one or more implants or portions thereof are inserted into the interior volume 604 of the targeted vertebral body 602, the implant augments the interior volume 604 and provides structural support to stabilize the vertebral body 602. In a vertebral body 602 that has collapsed, as the implant augments the interior volume 604, the implant may push against the inner sides of the endplates, thereby tending to restore the vertebral body 602 from a collapsed height to its original or desired treated height and provide structural support to stabilize the vertebral body 602. Instead of using the insertion of the implant to restore the height of the vertebral body 602, an instrument may be inserted through the passageway to restore the height of the vertebral endplates. For example, a balloon catheter may be inserted to restore the vertebral endplates, or an elongated instrument that contacts the inside of the endplates and pushes on them may be utilized. These techniques may also be utilized in combination to restore height of the vertebral body 602.

The flexibility of the implant allows bending of the implant within the interior volume 604, e.g., in a non-uniform or tortuous configuration, to aid in ensuring a thorough integration of the implant within the interior volume 604 of the targeted vertebral body 602, or potentially in a uniform pattern. The flexibility of the implant, as well as the configuration of the implant, may also permit bending of the implant to augment the interior volume 604 of the targeted vertebral body 602. The separation of the top and bottom members 20, 30 may also allow the implants to collapse and possibly become entangled so that it becomes larger than its insertion hole so that it cannot be easily ejected.

PMMA or another bone cement or filler (for example bone chips) may be inserted sequentially or simultaneously into the interior volume 604 of the targeted vertebral body 602 along with the implant to further enhance fixation or repair of the targeted vertebral body 602. Alternatively and/or in addition, a plug (not shown) of bone cement may be inserted into the passageway 610 that was initially formed to insert the implant. The plug may cover the insertion passageway 610 to prevent the implant from being removed or ejected. In other embodiments, some or all of the implant may be removed after repositioning the targeted vertebral body 602, and PMMA or another bone cement or filler may be injected into a void created by the implant. Alternatively a bone growth promoting filler may be inserted into the interior volume 604 and a plug of bone cement may be utilized to hold the implant and filler material in the vertebral body 602.

In some embodiments, the implant may be coated with an adhesive, such that the implant may be inserted into the targeted vertebral body 602 in a flexible state and may become tangled and/or convoluted during or after insertion. After insertion, the implant may become attached together by the adhesive so that the implant becomes a mass that may be locked into the interior volume 604 of the targeted vertebral body 602, or otherwise secured such that the implant may not be easily removed through the passageway 610.

In other embodiments, the implant may be coated with an adhesive and the implant may be inserted, with or without becoming tangled or convoluted, into the interior volume 604 of the targeted vertebral body 602. During or after insertion, some or all of the implant may be exposed to an energy source (e.g., an ultraviolet light, ultrasonic radiation, radio waves, heat, electric filed, magnetic field), for example to activate the adhesive, such that the exposed portion of implant becomes joined to form a mass, or becomes rigid, or both, thereby further augmenting the vertebral body 602 and/or preventing removal or ejection of the implant through the insertion opening.

Although the various embodiments of the flexible chain implants and methods described herein thus far have been described in the context of repositioning and augmenting a vertebral body 602, for example in the context of VCF and deformations in spinal curvature, various other uses and methods are envisioned. For example, in some embodiments, the implant may be used to augment a vertebral body 602 where a compression or a compression fracture has not yet occurred and thus may be preventative in nature. Also, in some embodiments the implant may be used between two vertebrae. For example, the implant may be inserted in the annulus of a spinal disc, or the disc may be removed and the implant inserted between adjacent vertebrae to promote fusion of adjacent vertebrae. The implant in some embodiments may be insertable in an additional implant, such as a cage implanted between adjacent vertebrae. The implant may also be used to reposition and/or augment other damaged bone regions such as a fractured or weakened proximal femur.

In some embodiments, the various embodiments of the flexible chain implants and methods described herein may be used in conjunction with other apparatus and methods to restore lordosis and augment the vertebral body 602. For example, one or more implants may be used in conjunction with known procedures that may be used to begin repositioning of a vertebral body 602 and/or to create a space within the vertebral body 602 for the implant. In other embodiments, one or more implants may be used in conjunction with other tools or external fixation apparatus for helping to manipulate or fix the vertebral body 602 or other bones in a desired position.

In another embodiment, a kit including various combinations of assemblies and components may include, for example, a cannula 1220, 606 or other introducer and one or more implants. The one or more implants may be provided in different sizes, e.g., different lengths and/or diameters. In other embodiments, the kit may include one or more of the following: an introducer, one or more implants, a syringe or other apparatus for injecting a cement or other filler into a vertebral body or other space, one or more balloon catheters, curettes, and other instruments and may additionally include anchoring elements, tensioning members, fixation members, or any combination thereof. One skilled in the art will appreciate that various other combinations of devices, components and assemblies may be made and are intended to fall within the scope of the present invention.

As described herein, the implants are preferably made from bone, more preferably allograft material, although use of xenograft and autograft is also envisioned. Furthermore, the implants described herein may be manufactured from materials with varying levels of porosity, such as by combining bone sections from different bones or different types of tissues and/or materials having varying levels of porosity.

Moreover, the implants, described herein, may be manufactured from bone materials having varying mineral content. For example, cancellous or cortical bone may be provided in natural, partially demineralized, or demineralized states. Variation in the mechanical properties of the bone sections used may be obtained through various amounts of demineralization. Advantageously, use of a demineralizing agent on bone, e.g., cortical or cancellous bone, transforms the properties of the bone from a stiff structure to a relatively pliable structure. Optionally, the flexibility or pliability of demineralized bone may be enhanced when the bone is hydrated. Any desired portions of the bone components may be demineralized or partially demineralized in order to achieve a desired amount of malleability, elasticity, pliability or flexibility, generally referred to herein as "flexibility." The amount of flexibility can be varied by varying in part the amount of demineralization.

In some embodiments, flexibility of demineralized or partially demineralized regions may be further enhanced by varying the moisture content of the implant, or portions thereof. Bone components initially may be provided with moisture content as follows: (a) bone in the natural state fresh out of the donor without freezing, (b) bone in the frozen state, typically at negative forty degrees Celsius (−40° C.), with moisture content intact, (c) bone with moisture removed such as freeze-dried bone, and (d) bone in the hydrated state, such as when submersed in water. Using the expansion and contraction properties that can be obtained during heating and cooling of the bone material, and the concomitant resorption of moisture along with swelling for some bone material, permits alternate approaches to achieving a desired flexibility of the implant within a bone or other region.

The implants may be formed entirely from cortical bone, entirely from cancellous bone, or from a combination of cortical and cancellous bone. While the implants may be created entirely from all bone material, it is also anticipated that one or more components or materials may be formed of non-bone material, including synthetics or other materials. Thus, while the implants, described herein, are typically described as being formed primarily from bone, the implants alternatively may be manufactured, in whole or in part, from any biocompatible material known in the art including, but not limited to, metals (such as, for example, stainless steel or titanium), alloys, hydroxyapatite, resorbable material, ceramics, polymers, composites, and encapsulated fluids, gels, etc.

One particular preferred alternate embodiment for manufacturing the implants described herein is a synthetic material. If the base synthetic material is naturally radiolucent then a radiopaque agent such as BaSO4 could be blended into the base material to make it visible on, for example, a C-arm image. The thin sections need only be thick enough so as to act as flexible "living hinges". Living hinge technology may be applied to the implants using a huge variation of plastic resins, such as polyethylene (PE), polypropylene (PP), and polycaprolactone (PCL). Plastics may offer the ability to be porous to promote bony in-growth or on-growth as well the ability to impregnate the base resin with pockets of chemicals, vitamins, medication, etc. that can release over time. Some resins are bioresorbable, such as, for example, PCL but others are not, such as, for example, PE, and it is possible that both characteristics could be useful in a bone void filler application depending on the indications. There are also some super-elastic metals such as Nitinol that may offer acceptable flexibility if the thin sections are designed small enough to be flexible and the thick sections are designed thick enough to add structural support to the tangled implant mass. Further, it is likely that a wide range of geometries and features can be included by using a synthetic material.

Additional applications of the above described implants can be realized in burst fractures, wherein extrapedicular or transpedicular placement of the implants can add stability during healing; prophylactic applications, wherein extrapedicular or transpedicular placement of the implants can be used within an intact (unfractured) vertebral body adjacent to a long-segment fusion or adjacent to an alternative bone stabilization construct, to provide additional stability as well as a more natural stiffness transition to the untreated levels when compared to the use of PMMA cement; interbody fusion extender, wherein placement of the implants within intervertebral spacers such as, for example, PLIF and TPLIF spacers to assist in fusion; and percutaneous placement of the implants within the lateral gutters to assist in fusing the posterolateral elements such as the adjacent transverse processes; and back filler material for iliac-crest autograft sites to help speed along the healing at this location and to reduce donor site morbidity.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A flexible chain implant configured to be inserted into an interior volume formed in a bone, the implant comprising:
   a top member having an outer surface and an inner surface; and
   a bottom member having an outer surface and an inner surface; the top and bottom members being coupled to one another, wherein the top and bottom members being constructed of bone, each of the inner surfaces of the top and bottom members include a plurality of alternating projections and recesses, and the projections of the top member are received within the recesses of the bottom member, the projections of the bottom member are received within the recesses of the top member, and
   the implant defines a first end and an opposed second terminal end, and the top and bottom members are coupled together at the first end when the implant is in an insertion position and an implanted configuration, and the top and bottom members are configured to separate from one another when in the implanted configuration.

2. The implant of claim 1, wherein the top and bottom members are formed of a monolithic portion of bone.

3. The implant of claim 1, wherein the top member is connected to the bottom member at the coupled portion.

4. The implant of claim 1, wherein the top and bottom members are coupled together at the coupled portion via a dovetail joint.

5. The implant of claim 4, wherein the top and bottom members are fixed together at the coupled portion by a demineralized dovetail joint.

6. The implant of claim 1, wherein the top and bottom members are fixed together at the coupled portion by a demineralized coupled portion.

7. The implant of claim 1, further comprising:
a cap having an engagement recess, the top member includes a first engagement projection at the coupled portion, the bottom member includes a second engagement projection at the coupled portion, the first and second engagement projections received within the engagement recess at the coupled portion in an assembled configuration, the cap configured to secure the top member to the bottom member in the assembled configuration.

8. The implant of claim 1, further comprising: a pin that couples the top and bottom members together at the coupled portion in an assembled configuration.

9. The implant of claim 8, wherein the top member includes a top engagement portion and the bottom member includes a bottom engagement portion, the top engagement portion having a top aperture and the bottom engagement portion having a bottom aperture, the top and bottom apertures receiving the pin in the assembled configuration.

10. The implant of claim 9, wherein the top member includes a stopper projection at the top engagement portion to prevent inadvertent removal of the pin in the assembled configuration.

11. The implant of claim 1, wherein the top member includes a longitudinal projection and the bottom member includes a longitudinal channel, the longitudinal projection received in the longitudinal channel in an assembled configuration.

12. The implant of claim 11, wherein the longitudinal projection is one of snap-fitted and slidably received into the longitudinal channel.

\* \* \* \* \*